(12) United States Patent
Chao et al.

(10) Patent No.: US 11,849,978 B2
(45) Date of Patent: *Dec. 26, 2023

(54) CONSTRAINED MOTION BONE SCREW ASSEMBLY

(71) Applicant: Medos International Sarl, Le Locle (CH)

(72) Inventors: Nam T. Chao, Marlborough, MA (US); Simon Siu, Quincy, MA (US); Ronald Sacher, Boca Raton, FL (US); Jerold P. Gurley, Middleburg Heights, OH (US); Randal Betz, Ocean City, NJ (US); Peter O. Newton, San Anselmo, CA (US)

(73) Assignee: Medos International Sarl, Le Locle (CH)

( * ) Notice: Subject to any disclaimer, the term of this patent is extended or adjusted under 35 U.S.C. 154(b) by 74 days.

This patent is subject to a terminal disclaimer.

(21) Appl. No.: 17/232,836

(22) Filed: Apr. 16, 2021

(65) Prior Publication Data

US 2021/0282818 A1 Sep. 16, 2021

Related U.S. Application Data

(63) Continuation of application No. 16/217,329, filed on Dec. 12, 2018, now Pat. No. 11,000,315, which is a (Continued)

(51) Int. Cl.
*A61B 17/70* (2006.01)
(52) U.S. Cl.
CPC ........ *A61B 17/7037* (2013.01); *A61B 17/704* (2013.01); *A61B 17/7038* (2013.01); *A61B 17/7041* (2013.01); *A61B 17/7032* (2013.01)

(58) Field of Classification Search
CPC .................... A61B 17/7037; A61B 17/7038
See application file for complete search history.

(56) References Cited

U.S. PATENT DOCUMENTS 410,780 A 9/1889 Cahn
445,513 A 1/1891 Powell
(Continued)

FOREIGN PATENT DOCUMENTS

DE 417480 C 8/1925
DE 3923996 A1 1/1991
(Continued)

OTHER PUBLICATIONS

European Office Action for Application No. 06735464.7, dated Feb. 10, 2012, 1-4.

(Continued)

*Primary Examiner* — Nicholas W Woodall
(74) *Attorney, Agent, or Firm* — Mintz Levin Cohn Ferris Glovsky and Popeo, P.C.

(57) ABSTRACT

A bone screw assembly includes an anchor portion and a head portion, such as a rod-receiving portion, movably mounted to the anchor portion to allow for controlled angulation between the anchor portion and the head portion. The anchor portion is pivotable in one or more selected directions about an axis relative to the head portion. A restriction member, which may be a rod seat, prevents the anchor portion from pivoting in one or more different directions about another axis relative to the head portion and/or a spinal fixation element received in the head portion. The restriction member may be inserted in the head portion to control direction that the anchor portion pivots relative to the head portion. The restriction member may also serve as a compression member and/or rod seat for seating a spinal rod coupled to the bone screw assembly.

18 Claims, 11 Drawing Sheets

Related U.S. Application Data continuation of application No. 15/711,380, filed on Sep. 21, 2017, now Pat. No. 10,172,648, which is a continuation of application No. 14/754,259, filed on Jun. 29, 2015, now Pat. No. 9,795,416, which is a continuation of application No. 11/073,325, filed on Mar. 4, 2005, now Pat. No. 7,951,172.

(56) References Cited

U.S. PATENT DOCUMENTS

| | | |
|---|---|---|
| 1,116,532 A | 11/1914 | Armstrong |
| 1,470,313 A | 10/1923 | Woolen |
| 1,628,144 A | 5/1927 | Herrmann |
| 1,709,766 A | 4/1929 | Bolton |
| 1,889,330 A | 11/1932 | Humes et al. |
| 1,925,385 A | 9/1933 | Humes et al. |
| 2,113,246 A | 4/1938 | Wappler |
| 2,248,054 A | 7/1941 | Becker |
| 2,248,057 A | 7/1941 | Bond |
| 2,291,413 A | 7/1942 | Siebrandt |
| 2,370,407 A | 2/1945 | Mccartney |
| 2,669,896 A | 2/1954 | Clough |
| 2,800,820 A | 7/1957 | Retterath |
| 2,952,285 A | 9/1960 | Roosli |
| 3,604,487 A | 9/1971 | Gilbert |
| 3,960,147 A | 6/1976 | Murray |
| 4,019,755 A | 4/1977 | Eisenhardt |
| 4,237,875 A | 12/1980 | Termanini |
| 4,271,836 A | 6/1981 | Bacal et al. |
| 4,363,250 A | 12/1982 | Suga |
| 4,411,259 A | 10/1983 | Drummond |
| 4,445,513 A | 5/1984 | Ulrich et al. |
| 4,655,223 A | 4/1987 | Kim |
| 4,733,657 A | 3/1988 | Kluger |
| 4,743,260 A | 5/1988 | Burton |
| 4,809,695 A | 3/1989 | Gwathmey et al. |
| 4,887,596 A | 12/1989 | Sherman |
| 4,896,661 A | 1/1990 | Bogert et al. |
| 4,950,269 A | 8/1990 | Gaines, Jr. |
| 4,957,495 A | 9/1990 | Kluger |
| 4,987,892 A | 1/1991 | Krag et al. |
| 5,005,562 A | 4/1991 | Cotrel |
| 5,014,407 A | 5/1991 | Boughten et al. |
| 5,020,519 A | 6/1991 | Hayes et al. |
| 5,067,955 A | 11/1991 | Cotrel |
| 5,092,866 A | 3/1992 | Breard et al. |
| 5,120,171 A | 6/1992 | Lasner |
| 5,176,678 A | 1/1993 | Tsou |
| 5,176,680 A | 1/1993 | Vignaud et al. |
| 5,181,917 A | 1/1993 | Rogozinski |
| 5,181,971 A | 1/1993 | Ohtsuka |
| 5,190,543 A | 3/1993 | Schlaepfer |
| 5,219,349 A | 6/1993 | Krag et al. |
| 5,226,766 A | 7/1993 | Lasner |
| 5,261,913 A | 11/1993 | Marnay |
| 5,263,939 A | 11/1993 | Wortrich |
| 5,282,801 A | 2/1994 | Sherman |
| 5,282,863 A | 2/1994 | Burton |
| D346,217 S | 4/1994 | Sparker et al. |
| 5,306,248 A | 4/1994 | Barrington |
| 5,330,474 A | 7/1994 | Lin |
| 5,334,203 A | 8/1994 | Wagner |
| 5,360,431 A | 11/1994 | Puno et al. |
| 5,364,397 A | 11/1994 | Hayes et al. |
| 5,385,565 A | 1/1995 | Ray |
| 5,387,213 A | 2/1995 | Breard et al. |
| 5,391,170 A | 2/1995 | Mcguire et al. |
| 5,415,661 A | 5/1995 | Holmes |
| 5,429,641 A | 7/1995 | Gotfried |
| 5,431,658 A | 7/1995 | Moskovich |
| 5,468,241 A | 11/1995 | Metz-stavenhagen et al. |
| 5,478,340 A | 12/1995 | Kluger |
| 5,484,440 A | 1/1996 | Allard |
| 5,487,744 A | 1/1996 | Howland |
| 5,499,983 A | 3/1996 | Hughes |
| 5,501,684 A | 3/1996 | Schlapfer et al. |
| 5,520,689 A | 5/1996 | Schlaepfer et al. |
| 5,522,816 A | 6/1996 | Dinello et al. |
| 5,536,127 A | 7/1996 | Pennig |
| 5,536,268 A | 7/1996 | Griss |
| 5,540,688 A | 7/1996 | Navas |
| 5,545,165 A | 8/1996 | Harms et al. |
| 5,549,608 A | 8/1996 | Errico et al. |
| 5,551,320 A | 9/1996 | Horobec et al. |
| 5,591,166 A | 1/1997 | Bernhardt et al. |
| 5,591,235 A | 1/1997 | Kuslich |
| 5,616,143 A | 4/1997 | Schlapfer et al. |
| 5,649,931 A | 7/1997 | Bryant et al. |
| 5,667,513 A | 9/1997 | Torrie et al. |
| 5,672,175 A | 9/1997 | Martin |
| 5,672,176 A | 9/1997 | Biedermann et al. |
| 5,683,399 A | 11/1997 | Jones |
| 5,697,933 A | 12/1997 | Gundlapalli et al. |
| 5,702,393 A | 12/1997 | Pfaifer |
| 5,707,371 A | 1/1998 | Metz-stavenhagen |
| 5,720,751 A | 2/1998 | Jackson |
| 5,725,532 A | 3/1998 | Shoemaker |
| 5,746,757 A | 5/1998 | Mcguire |
| 5,782,831 A | 7/1998 | Sherman et al. |
| 5,797,910 A | 8/1998 | Martin |
| 5,797,911 A | 8/1998 | Sherman et al. |
| 5,810,878 A | 9/1998 | Burel et al. |
| 5,814,046 A | 9/1998 | Hopf |
| 5,879,350 A | 3/1999 | Sherman et al. |
| 5,882,350 A | 3/1999 | Ralph et al. |
| 5,885,285 A | 3/1999 | Simonson |
| RE36,211 E | 5/1999 | Nonomura |
| RE36,221 E | 6/1999 | Breard et al. |
| 5,910,141 A | 6/1999 | Morrison et al. |
| 5,938,663 A | 8/1999 | Petreto |
| 5,941,885 A | 8/1999 | Jackson |
| 5,951,555 A | 9/1999 | Rehak et al. |
| 5,951,564 A | 9/1999 | Schroder et al. |
| 5,951,579 A | 9/1999 | Dykes |
| 5,964,760 A | 10/1999 | Richelsoph |
| 5,976,133 A | 11/1999 | Kraus et al. |
| 5,989,250 A | 11/1999 | Wagner et al. |
| 5,989,254 A | 11/1999 | Katz |
| 6,010,509 A | 1/2000 | Delgado et al. |
| 6,036,692 A | 3/2000 | Burel et al. |
| 6,050,997 A | 4/2000 | Mullane |
| 6,063,090 A | 5/2000 | Schlaepfer |
| 6,074,391 A | 6/2000 | Metz-stavenhagen et al. |
| 6,090,110 A | 7/2000 | Metz-stavenhagen |
| 6,090,113 A | 7/2000 | Le et al. |
| 6,099,528 A | 8/2000 | Saurat |
| 6,123,707 A | 9/2000 | Wagner |
| 6,139,549 A | 10/2000 | Keller |
| 6,146,383 A | 11/2000 | Studer et al. |
| 6,183,472 B1 | 2/2001 | Lutz |
| 6,189,422 B1 | 2/2001 | Stihl |
| 6,204,060 B1 | 3/2001 | Mehtali et al. |
| 6,210,330 B1 | 4/2001 | Tepper |
| 6,235,028 B1 | 5/2001 | Brumfield et al. |
| 6,251,112 B1 | 6/2001 | Jackson |
| 6,254,602 B1 | 7/2001 | Justis |
| 6,258,090 B1 | 7/2001 | Jackson |
| 6,261,287 B1 | 7/2001 | Metz-stavenhagen |
| 6,280,442 B1 | 8/2001 | Barker et al. |
| 6,280,443 B1 | 8/2001 | Gu et al. |
| 6,287,309 B1 | 9/2001 | Baccelli et al. |
| 6,299,616 B1 | 10/2001 | Beger |
| 6,302,888 B1 | 10/2001 | Mellinger et al. |
| 6,309,389 B1 | 10/2001 | Baccelli |
| 6,368,321 B1 | 4/2002 | Jackson |
| 6,371,973 B1 | 4/2002 | Tepper |
| 6,379,357 B1 | 4/2002 | Bernstein et al. |
| 6,402,752 B2 | 6/2002 | Schaeffler-wachter et al. |
| 6,423,065 B2 | 7/2002 | Ferree |
| 6,440,133 B1 | 8/2002 | Beale et al. |
| 6,440,137 B1 | 8/2002 | Horvath et al. |
| 6,440,142 B1 | 8/2002 | Ralph et al. |
| 6,440,144 B1 | 8/2002 | Bacher |
| 6,443,953 B1 | 9/2002 | Perra et al. |

(56) References Cited

U.S. PATENT DOCUMENTS

| | | |
|---|---|---|
| 6,478,798 B1 | 11/2002 | Howland |
| 6,511,484 B2 | 1/2003 | Torode et al. |
| 6,530,929 B1 | 3/2003 | Justis et al. |
| 6,537,276 B2 | 3/2003 | Metz-stavenhagen |
| 6,540,748 B2 | 4/2003 | Lombardo |
| 6,554,831 B1 | 4/2003 | Rivard et al. |
| 6,565,567 B1 | 5/2003 | Haider |
| 6,589,249 B2 | 7/2003 | Sater et al. |
| 6,597,279 B1 | 7/2003 | Haraguchi |
| 6,623,485 B2 | 9/2003 | Doubler et al. |
| 6,648,888 B1 | 11/2003 | Shluzas |
| 6,652,523 B1 | 11/2003 | Evrard et al. |
| 6,660,006 B2 | 12/2003 | Markworth et al. |
| 6,689,137 B2 | 2/2004 | Reed |
| 6,692,500 B2 | 2/2004 | Reed |
| 6,695,843 B2 | 2/2004 | Biedermann et al. |
| 6,716,214 B1 | 4/2004 | Jackson |
| 6,726,692 B2 | 4/2004 | Bette |
| 6,733,502 B2 | 5/2004 | Altarac et al. |
| 6,743,231 B1 | 6/2004 | Gray et al. |
| 6,746,449 B2 | 6/2004 | Jones et al. |
| 6,749,613 B1 | 6/2004 | Conchy et al. |
| 6,752,832 B2 | 6/2004 | Neumann |
| 6,755,829 B1 | 6/2004 | Bono et al. |
| 6,783,527 B2 | 8/2004 | Drewry et al. |
| 6,790,208 B2 | 9/2004 | Oribe et al. |
| 6,790,209 B2 | 9/2004 | Beale et al. |
| 6,800,078 B2 | 10/2004 | Reed |
| 6,800,079 B2 | 10/2004 | Reed |
| 6,827,722 B1 | 12/2004 | Schoenefeld et al. |
| 6,837,889 B2 | 1/2005 | Shluzas |
| 6,964,666 B2 | 11/2005 | Jackson |
| 7,081,117 B2 | 7/2006 | Bono et al. |
| 7,083,621 B2 | 8/2006 | Shaolian et al. |
| 7,090,677 B2 | 8/2006 | Fallin et al. |
| 7,156,849 B2 | 1/2007 | Dunbar et al. |
| 7,160,300 B2 | 1/2007 | Jackson |
| 7,179,254 B2 | 2/2007 | Pendekanti et al. |
| 7,179,261 B2 | 2/2007 | Sicvol et al. |
| 7,189,234 B2 | 3/2007 | Zucherman et al. |
| 7,250,052 B2 | 7/2007 | Landry et al. |
| 7,278,995 B2 | 10/2007 | Nichols et al. |
| 7,320,689 B2 | 1/2008 | Keller |
| 7,322,979 B2 | 1/2008 | Crandall et al. |
| 7,371,239 B2 | 5/2008 | Dec et al. |
| 7,455,685 B2 | 11/2008 | Justis |
| 7,462,182 B2 | 12/2008 | Lim |
| 7,465,306 B2 | 12/2008 | Pond et al. |
| 7,470,279 B2 | 12/2008 | Jackson |
| 7,485,120 B2 | 2/2009 | Ray |
| 7,491,207 B2 | 2/2009 | Keyer et al. |
| 7,491,208 B2 | 2/2009 | Pond et al. |
| 7,491,218 B2 | 2/2009 | Landry et al. |
| 7,527,638 B2 | 5/2009 | Anderson et al. |
| 7,572,281 B2 | 8/2009 | Runco et al. |
| 7,588,585 B2 | 9/2009 | Gold et al. |
| 7,591,836 B2 | 9/2009 | Dick et al. |
| 7,621,918 B2 | 11/2009 | Jackson |
| 7,651,502 B2 | 1/2010 | Jackson |
| 7,666,188 B2 | 2/2010 | Anderson et al. |
| 7,666,189 B2 | 2/2010 | Gerber et al. |
| 7,708,736 B2 | 5/2010 | Mullaney |
| 7,708,763 B2 | 5/2010 | Selover et al. |
| 7,766,944 B2 | 8/2010 | Metz-stavenhagen |
| 7,794,464 B2 | 9/2010 | Bridwell et al. |
| 7,824,411 B2 | 11/2010 | Varieur et al. |
| 7,824,413 B2 | 11/2010 | Varieur et al. |
| 7,842,044 B2 | 11/2010 | Runco et al. |
| 7,867,237 B2 | 1/2011 | Stad et al. |
| 7,887,539 B2 | 2/2011 | Dunbar et al. |
| 7,887,541 B2 | 2/2011 | Runco et al. |
| 7,951,168 B2 | 5/2011 | Chao et al. |
| 7,951,172 B2 | 5/2011 | Chao et al. |
| 7,951,175 B2 | 5/2011 | Chao et al. |
| 7,981,172 B2 | 7/2011 | Edlund et al. |
| 7,988,698 B2 | 8/2011 | Rosenberg et al. |
| 8,007,516 B2 | 8/2011 | Chao et al. |
| 8,172,847 B2 | 5/2012 | Dziedzic et al. |
| 8,192,438 B2 | 6/2012 | Garamszegi |
| 8,216,241 B2 | 7/2012 | Runco et al. |
| 8,608,746 B2 | 12/2013 | Kolb et al. |
| 8,647,347 B2 | 2/2014 | Runco et al. |
| 8,709,044 B2 | 4/2014 | Chao et al. |
| 8,845,700 B2 | 9/2014 | Kwak et al. |
| 8,888,777 B2 | 11/2014 | Mullaney |
| 9,095,379 B2 | 8/2015 | Chao et al. |
| 9,326,798 B2 | 5/2016 | Kolb et al. |
| 9,795,416 B2 | 10/2017 | Chao et al. |
| 10,172,648 B2 | 1/2019 | Chao et al. |
| 10,314,624 B2 | 6/2019 | Chao et al. |
| 11,000,315 B2 | 5/2021 | Chao et al. |
| 2001/0020169 A1 | 9/2001 | Metz-stavenhagen |
| 2001/0029376 A1 | 10/2001 | Sater et al. |
| 2002/0035366 A1 | 3/2002 | Walder et al. |
| 2002/0072752 A1 | 6/2002 | Zucherman et al. |
| 2002/0082599 A1 | 6/2002 | Crandall et al. |
| 2002/0095153 A1 | 7/2002 | Jones et al. |
| 2002/0133155 A1 | 9/2002 | Ferree |
| 2002/0143341 A1* | 10/2002 | Biedermann ...... A61B 17/7035 606/308 |
| 2002/0151900 A1 | 10/2002 | Glascott |
| 2002/0173789 A1 | 11/2002 | Howland |
| 2003/0009168 A1 | 1/2003 | Beale et al. |
| 2003/0028195 A1 | 2/2003 | Bette |
| 2003/0045875 A1 | 3/2003 | Bertranou et al. |
| 2003/0073995 A1 | 4/2003 | Reed |
| 2003/0083657 A1 | 5/2003 | Drewry et al. |
| 2003/0083747 A1 | 5/2003 | Winterbottom et al. |
| 2003/0088248 A1 | 5/2003 | Reed |
| 2003/0100896 A1 | 5/2003 | Biedermann et al. |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0125750 A1 | 7/2003 | Zwirnmann et al. |
| 2003/0149438 A1 | 8/2003 | Nichols et al. |
| 2003/0171749 A1 | 9/2003 | Le et al. |
| 2003/0171756 A1 | 9/2003 | Fallin et al. |
| 2003/0176861 A1 | 9/2003 | Reed |
| 2003/0191370 A1 | 10/2003 | Phillips |
| 2003/0191470 A1 | 10/2003 | Ritland |
| 2003/0199872 A1 | 10/2003 | Markworth et al. |
| 2003/0203488 A1 | 10/2003 | Mehtali et al. |
| 2003/0220642 A1 | 11/2003 | Freudiger |
| 2003/0220643 A1 | 11/2003 | Ferree |
| 2003/0225408 A1 | 12/2003 | Nichols et al. |
| 2004/0002708 A1 | 1/2004 | Ritland |
| 2004/0036254 A1 | 2/2004 | Patton |
| 2004/0049189 A1 | 3/2004 | Le et al. |
| 2004/0049190 A1 | 3/2004 | Biedermann et al. |
| 2004/0049191 A1 | 3/2004 | Markworth et al. |
| 2004/0073215 A1 | 4/2004 | Carli |
| 2004/0092931 A1 | 5/2004 | Taylor et al. |
| 2004/0102789 A1 | 5/2004 | Baughman |
| 2004/0147936 A1 | 7/2004 | Rosenberg et al. |
| 2004/0147937 A1 | 7/2004 | Dunbar et al. |
| 2004/0158257 A1 | 8/2004 | Bonati et al. |
| 2004/0158258 A1 | 8/2004 | Bonati et al. |
| 2004/0172025 A1 | 9/2004 | Drewry et al. |
| 2004/0172057 A1 | 9/2004 | Guillebon et al. |
| 2004/0176779 A1 | 9/2004 | Casutt et al. |
| 2004/0181224 A1 | 9/2004 | Biedermann et al. |
| 2004/0186473 A1 | 9/2004 | Cournoyer et al. |
| 2004/0204711 A1 | 10/2004 | Jackson |
| 2004/0220567 A1 | 11/2004 | Eisermann et al. |
| 2004/0225289 A1 | 11/2004 | Biedermann et al. |
| 2004/0243139 A1 | 12/2004 | Lewis et al. |
| 2004/0254576 A1 | 12/2004 | Dunbar et al. |
| 2004/0267260 A1 | 12/2004 | Mack et al. |
| 2004/0267264 A1 | 12/2004 | Konieczynski et al. |
| 2004/0267275 A1 | 12/2004 | Cournoyer et al. |
| 2005/0015094 A1 | 1/2005 | Keller |
| 2005/0015095 A1 | 1/2005 | Keller |
| 2005/0021031 A1 | 1/2005 | Foley et al. |
| 2005/0033291 A1 | 2/2005 | Ebara |

(56) References Cited

U.S. PATENT DOCUMENTS

| | | |
|---|---|---|
| 2005/0033295 A1 | 2/2005 | Wisnewski |
| 2005/0033299 A1 | 2/2005 | Shluzas |
| 2005/0055031 A1 | 3/2005 | Lim |
| 2005/0059969 A1 | 3/2005 | Mckinley |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0070917 A1 | 3/2005 | Justis |
| 2005/0079909 A1 | 4/2005 | Singhaseni |
| 2005/0085813 A1 | 4/2005 | Spitler et al. |
| 2005/0085815 A1 | 4/2005 | Harms et al. |
| 2005/0090824 A1 | 4/2005 | Shluzas et al. |
| 2005/0131408 A1 | 6/2005 | Sicvol et al. |
| 2005/0131420 A1 | 6/2005 | Techiera et al. |
| 2005/0131421 A1 | 6/2005 | Anderson et al. |
| 2005/0131422 A1 | 6/2005 | Anderson et al. |
| 2005/0137593 A1 | 6/2005 | Gray et al. |
| 2005/0143737 A1 | 6/2005 | Pafford et al. |
| 2005/0143749 A1 | 6/2005 | Zalenski et al. |
| 2005/0149036 A1 | 7/2005 | Varieur et al. |
| 2005/0149048 A1 | 7/2005 | Leport et al. |
| 2005/0149053 A1 | 7/2005 | Varieur et al. |
| 2005/0154389 A1 | 7/2005 | Selover et al. |
| 2005/0159650 A1 | 7/2005 | Raymond et al. |
| 2005/0177163 A1 | 8/2005 | Abdou |
| 2005/0192570 A1 | 9/2005 | Jackson |
| 2005/0192573 A1 | 9/2005 | Abdelgany et al. |
| 2005/0192579 A1 | 9/2005 | Jackson |
| 2005/0192589 A1 | 9/2005 | Raymond et al. |
| 2005/0222570 A1 | 10/2005 | Jackson |
| 2005/0228376 A1 | 10/2005 | Boomer et al. |
| 2005/0228380 A1 | 10/2005 | Moore et al. |
| 2005/0228392 A1 | 10/2005 | Keyer et al. |
| 2005/0228400 A1 | 10/2005 | Chao et al. |
| 2005/0234449 A1 | 10/2005 | Aferzon |
| 2005/0245928 A1 | 11/2005 | Colleran et al. |
| 2005/0261687 A1* | 11/2005 | Garamszegi ....... A61B 17/8605 606/328 |
| 2005/0261702 A1 | 11/2005 | Oribe et al. |
| 2005/0283244 A1 | 12/2005 | Gordon et al. |
| 2005/0288668 A1 | 12/2005 | Brinkhaus |
| 2006/0009775 A1 | 1/2006 | Dec et al. |
| 2006/0025768 A1 | 2/2006 | Iott et al. |
| 2006/0036254 A1 | 2/2006 | Lim |
| 2006/0036255 A1 | 2/2006 | Pond et al. |
| 2006/0036260 A1 | 2/2006 | Runco et al. |
| 2006/0069391 A1 | 3/2006 | Jackson |
| 2006/0074418 A1 | 4/2006 | Jackson |
| 2006/0079909 A1 | 4/2006 | Runco et al. |
| 2006/0089651 A1 | 4/2006 | Trudeau et al. |
| 2006/0095035 A1 | 5/2006 | Jones et al. |
| 2006/0111712 A1 | 5/2006 | Jackson |
| 2006/0111713 A1 | 5/2006 | Jackson |
| 2006/0111730 A1 | 5/2006 | Hay |
| 2006/0149236 A1 | 7/2006 | Barry |
| 2006/0155277 A1 | 7/2006 | Metz-stavenhagen |
| 2006/0166534 A1 | 7/2006 | Brumfield et al. |
| 2006/0166535 A1 | 7/2006 | Brumfield et al. |
| 2006/0173454 A1 | 8/2006 | Spitler et al. |
| 2006/0195092 A1 | 8/2006 | Barry |
| 2006/0200131 A1 | 9/2006 | Chao et al. |
| 2006/0200132 A1 | 9/2006 | Chao et al. |
| 2006/0217735 A1 | 9/2006 | Macdonald et al. |
| 2006/0229605 A1 | 10/2006 | Olsen |
| 2006/0229614 A1 | 10/2006 | Foley et al. |
| 2006/0247630 A1 | 11/2006 | Iott et al. |
| 2006/0264934 A1 | 11/2006 | Fallin |
| 2006/0271050 A1 | 11/2006 | Piza |
| 2006/0282073 A1 | 12/2006 | Simanovsky |
| 2006/0293690 A1 | 12/2006 | Abdelgany |
| 2006/0293692 A1 | 12/2006 | Whipple et al. |
| 2007/0078460 A1 | 4/2007 | Frigg et al. |
| 2007/0093849 A1 | 4/2007 | Jones et al. |
| 2007/0100347 A1 | 5/2007 | Stad et al. |
| 2007/0118118 A1 | 5/2007 | Kwak et al. |
| 2007/0129731 A1 | 6/2007 | Sicvol et al. |
| 2007/0161994 A1 | 7/2007 | Lowery et al. |
| 2007/0161998 A1 | 7/2007 | Whipple |
| 2007/0162009 A1 | 7/2007 | Chao et al. |
| 2007/0162010 A1 | 7/2007 | Chao et al. |
| 2007/0167954 A1 | 7/2007 | Sicvol et al. |
| 2007/0173831 A1 | 7/2007 | Abdou |
| 2007/0185375 A1 | 8/2007 | Stad et al. |
| 2007/0191836 A1 | 8/2007 | Justis |
| 2007/0213715 A1 | 9/2007 | Bridwell et al. |
| 2007/0213716 A1 | 9/2007 | Lenke et al. |
| 2007/0213722 A1 | 9/2007 | Jones et al. |
| 2007/0231059 A1 | 10/2007 | Mullaney |
| 2007/0233079 A1 | 10/2007 | Fallin et al. |
| 2007/0233097 A1 | 10/2007 | Anderson et al. |
| 2007/0260261 A1 | 11/2007 | Runco et al. |
| 2007/0270880 A1 | 11/2007 | Lindemann et al. |
| 2007/0282337 A1 | 12/2007 | Garamszegi |
| 2008/0045956 A1 | 2/2008 | Songer et al. |
| 2008/0077134 A1 | 3/2008 | Dziedzic et al. |
| 2008/0077135 A1 | 3/2008 | Stad et al. |
| 2008/0086130 A1 | 4/2008 | Lake et al. |
| 2008/0161853 A1 | 7/2008 | Arnold et al. |
| 2008/0161863 A1 | 7/2008 | Arnold et al. |
| 2008/0172062 A1 | 7/2008 | Donahue et al. |
| 2008/0195159 A1 | 8/2008 | Kloss et al. |
| 2008/0243190 A1 | 10/2008 | Dziedzic et al. |
| 2008/0255574 A1 | 10/2008 | Dye |
| 2008/0288005 A1 | 11/2008 | Jackson |
| 2009/0005815 A1 | 1/2009 | Ely |
| 2009/0018541 A1 | 1/2009 | Lavi |
| 2009/0030419 A1 | 1/2009 | Runco et al. |
| 2009/0030420 A1 | 1/2009 | Runco et al. |
| 2009/0054902 A1 | 2/2009 | Hawkins et al. |
| 2009/0062857 A1 | 3/2009 | Ramsay et al. |
| 2009/0082811 A1 | 3/2009 | Stad et al. |
| 2009/0088764 A1 | 4/2009 | Paiva et al. |
| 2009/0138056 A1 | 5/2009 | Anderson et al. |
| 2009/0143828 A1 | 6/2009 | Stad et al. |
| 2009/0228051 A1 | 9/2009 | Kolb et al. |
| 2009/0228053 A1 | 9/2009 | Kolb et al. |
| 2009/0281579 A1 | 11/2009 | Weaver et al. |
| 2010/0045155 A1 | 2/2010 | Padilla |
| 2010/0063544 A1 | 3/2010 | Butler |
| 2010/0137915 A1 | 6/2010 | Anderson et al. |
| 2011/0034961 A1 | 2/2011 | Runco et al. |
| 2011/0034962 A1 | 2/2011 | Dunbar et al. |
| 2011/0077689 A1 | 3/2011 | Mickiewicz et al. |
| 2011/0093022 A1 | 4/2011 | Runco et al. |
| 2011/0144695 A1 | 6/2011 | Rosenberg et al. |
| 2011/0196431 A1 | 8/2011 | Chao et al. |
| 2011/0282402 A1 | 11/2011 | Chao et al. |
| 2012/0253413 A1 | 10/2012 | Runco et al. |
| 2014/0188182 A1 | 7/2014 | Chao et al. |
| 2014/0277198 A1 | 9/2014 | Stad |
| 2015/0297268 A1 | 10/2015 | Chao et al. |
| 2017/0156765 A1 | 6/2017 | Chao et al. |
| 2018/0008319 A1 | 1/2018 | Chao et al. |
| 2019/0216509 A1 | 7/2019 | Chao et al. |
| 2019/0307492 A1 | 10/2019 | Chao et al. |

FOREIGN PATENT DOCUMENTS

| | | |
|---|---|---|
| DE | 9110203 U1 | 11/1991 |
| DE | 4107480 A1 | 9/1992 |
| DE | 4238339 A1 | 5/1994 |
| DE | 29806563 U1 | 6/1998 |
| DE | 10005385 A1 | 8/2001 |
| DE | 10005386 A1 | 8/2001 |
| DE | 20207851 U1 | 10/2002 |
| EP | 0487895 A1 | 6/1992 |
| EP | 0558883 A1 | 9/1993 |
| EP | 0441729 B1 | 1/1994 |
| EP | 0592266 A1 | 4/1994 |
| EP | 0328883 B1 | 7/1994 |
| EP | 0572790 B1 | 2/1996 |
| EP | 0885598 A2 | 12/1998 |
| EP | 0669109 B1 | 5/1999 |

(56) References Cited

FOREIGN PATENT DOCUMENTS

| | | |
|---|---|---|
| EP | 0948939 A2 | 10/1999 |
| EP | 0381588 B2 | 5/2000 |
| EP | 1023873 A2 | 8/2000 |
| EP | 1090595 A2 | 4/2001 |
| EP | 0784693 B1 | 10/2001 |
| EP | 1295566 A1 | 3/2003 |
| EP | 0951246 81 | 5/2003 |
| EP | 0880344 81 | 8/2003 |
| EP | 1364622 B1 | 7/2005 |
| EP | 1574175 A1 | 9/2005 |
| FR | 2677242 A1 | 12/1992 |
| FR | 2680314 A1 | 2/1993 |
| FR | 2729291 A1 | 7/1996 |
| JP | 2003052708 A | 2/2003 |
| JP | 2007525274 A | 9/2007 |
| WO | 9002527 | 3/1990 |
| WO | 9621396 A1 | 7/1996 |
| WO | 9822033 A1 | 5/1998 |
| WO | 9825534 A1 | 6/1998 |
| WO | 9944527 A1 | 9/1999 |
| WO | 0145576 A1 | 6/2001 |
| WO | 0207622 A1 | 1/2002 |
| WO | 02102259 A2 | 12/2002 |
| WO | 03007828 A1 | 1/2003 |
| WO | 03032863 A2 | 4/2003 |
| WO | 03049629 A1 | 6/2003 |
| WO | 03096915 A1 | 11/2003 |
| WO | 2004004549 A2 | 1/2004 |
| WO | 2004019755 A2 | 3/2004 |
| WO | 2004034916 A1 | 4/2004 |
| WO | 2005006948 A2 | 1/2005 |
| WO | 2005013839 A2 | 2/2005 |
| WO | 2005030065 A1 | 4/2005 |
| WO | 2005044117 A2 | 5/2005 |
| WO | 2005044123 A1 | 5/2005 |
| WO | 2005072081 A2 | 8/2005 |
| WO | 2006020443 A1 | 2/2006 |
| WO | 2006084443 A1 | 8/2006 |
| WO | 2007092797 A2 | 8/2007 |
| WO | 2007092870 A2 | 8/2007 |
| WO | 2007092876 A2 | 8/2007 |
| WO | 2007149426 A2 | 12/2007 |
| WO | 2008024937 A2 | 2/2008 |

OTHER PUBLICATIONS

European Office Action for Application No. 06735464.7, dated Apr. 14, 2010.
European Office Action for Application No. 06736870, dated Dec. 18, 2009.
International Preliminary Report on Patentability issued in International Patent Application No. PCT/US2006/005811, dated Oct. 9, 2007, 8 pages.
International Search Report and Written Opinion for Application No. PCT/US06/40621, dated May 18, 2007.
International Search Report and Written Opinion issued in International Application No. PCT/US06/07619, dated Apr. 16, 2007, 3 pages.
International Search Report and Written Opinion issued in International Application No. PCT/US2006/005811, dated Sep. 13, 2007, 10 pages.
International Search Report issued in International Application No. PCT/US2008/068515, dated Jan. 2, 2009.
Sofamor Introducteur Contreur De Tige, Jun. 1994.
Supplementary European Search Report issued in European Application No. 06735464.7, dated Apr. 14, 2010, 10 pages.
Wiltse et al., 1992, "History of Pedicle Screw Fixation of the Spine", Spine, State of the Art Reviews, 6(1):1-10.

* cited by examiner

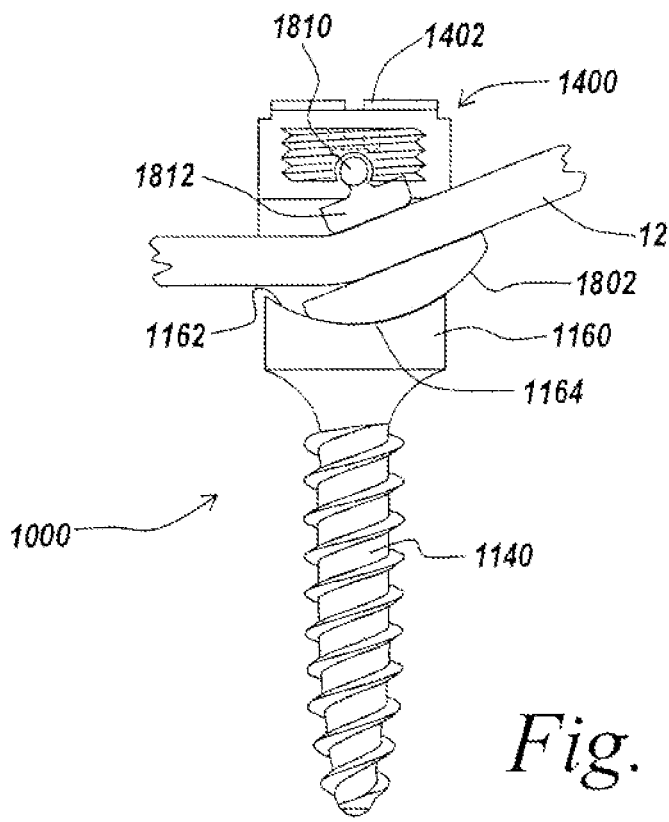
Fig. 13C
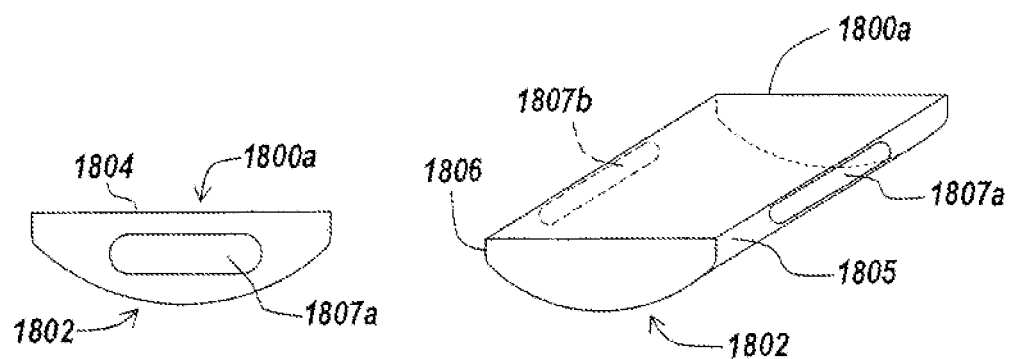
Fig. 14A
Fig. 14B

CONSTRAINED MOTION BONE SCREW ASSEMBLY

RELATED APPLICATIONS

The present application is a continuation application of U.S. application Ser. No. 16/217,329 filed on Dec. 12, 2018, entitled "Constrained Motion Bone Screw Assembly," which is a continuation to U.S. application Ser. No. 15/711,380 (now U.S. Pat. No. 10,172,648) filed on Sep. 21, 2017, entitled "Constrained Motion Bone Screw Assembly," which is a continuation to U.S. application Ser. No. 14/754,259 (now U.S. Pat. No. 9,795,416), filed on Jun. 29, 2015, entitled "Constrained Motion Bone Screw Assembly," which is a continuation to U.S. application Ser. No. 11/073,325 (now U.S. Pat. No. 7,951,172) filed on Mar. 4, 2005, entitled "Constrained Motion Bone Screw Assembly," the contents of which are hereby incorporated herein by reference in their entireties.

FIELD OF THE INVENTION

The present invention relates to spinal fixation devices used in orthopedic surgery. More particularly, the present invention relates to a bone screw for coupling a spinal rod to a bone, such as the pedicle.

BACKGROUND OF THE INVENTION

Spinal fixation systems may be used in surgery to align, adjust and/or fix portions of the spinal column, i.e., vertebrae, in a desired spatial relationship relative to each other. Many spinal fixation systems employ a spinal rod for supporting the spine and for properly positioning components of the spine for various treatment purposes. Vertebral anchors, comprising pins, bolts, screws, and hooks, engage the vertebrae and connect the supporting rod to different vertebrae. The size, length and shape of the cylindrical rod depend on the size, number and position of the vertebrae to be held in a desired spatial relationship relative to each other by the apparatus.

Spinal fixation elements can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a spinal fixation element-receiving element, which, in spinal rod applications, is usually in the form of a U-shaped slot formed in the head portion for receiving the rod. A set-screw, plug, cap or similar type of closure mechanism is used to lock the rod into the rod-receiving portion of the pedicle screw. In use, the shank portion of each screw is then threaded into a vertebra, and once properly positioned, a fixation rod is seated through the rod-receiving portion of each screw. The rod is locked into place by tightening a cap or similar type of closure mechanism to securely interconnect each screw and the fixation rod. Other anchoring devices also include hooks and other types of bone screws.

Monoaxial screws are a type of screw in which the longitudinal axis of the threaded shank is fixed relative to the head portion, or rod slot. The longitudinal axis of the threaded shank may be aligned with the longitudinal axis of the head portion, and/or the threaded shank extends at a fixed angle relative to the head. In fixed pedicle screws, which are used in the pedicle region of the vertebra, the threaded shank is rigidly connected to or integrally formed with the head such that the orientation of the threaded shank is fixed with respect to the head.

Polyaxial pedicle screws have been designed to allow angulation of one portion of the screw relative to another portion of the screw and the spinal fixation element coupled to one portion of the screw. For example, polyaxial pedicle screws allow for a shaft portion to pivot relative to a rod-receiving portion in all directions about a 360° arc around the rod-receiving portion. Polyaxial screws may be useful for positioning bone anchors on adjacent vertebrae, when the close proximity of adjacent vertebrae can result in interference between the bone anchors. Polyaxial screws allow for pivoting of the screws in any direction out of alignment with each other to avoid such interference.

An example of such a polyaxial pedicle screw assembly is described in detail in U.S. Patent Application Publication Number US 2004/0186473 entitled "Spinal Fixation Devices of Improved Strength and Rigidity", U.S. Patent Application Publication Number US 2004/0181224 entitled "Anchoring Element for Use in Spine or Bone Surgery, Methods for Use and Production Thereof" and U.S. Patent Application Publication Number US 2003/0100896, entitled "Element With a Shank and a Holding Element Connected to It for Connecting to a Rod", the contents of which are herein incorporated by reference.

Polyaxial and multi-axial screws, which allow the screw shank to pivot in all directions about the head portion, can be difficult to control and often result in movement of the screw shank in planes in which movement is not desirable. For example, during vertebral body rotation maneuvers, which require application of force to the screw head, it is not desirable for the screw shank to move relative to the screw head.

SUMMARY OF THE INVENTION

The present invention provides a bone screw assembly that provides for controlled movement between an anchor portion and a rod-receiving portion of the bone screw assembly. The bone screw assembly allows the anchor portion to pivot about the rod-receiving portion and/or a spinal fixation element received in the rod-receiving portion in one or more directions, while limiting the movement in other selected directions. For example, the anchor portion can pivot about a first axis that passes through the head of the anchor portion and is perpendicular to a longitudinal axis of a rod received in the rod-receiving portion, so that the anchor portion aligns with the rod in a selected plane, while being restricted from rotation about one or more other axes of the head. When assembled in a patient, the anchor portion may be moveable in at least one plane, such as the coronal plane, to allow for movement of vertebral bodies coupled to the rod by the bone screw assembly in one or more selected directions, while fixed in at least one plane, such as the sagittal plane, to prevent movement in one or more other directions.

According to a first aspect of the invention, a bone anchor assembly comprises a bone anchor having a proximal head and a distal shaft extending along a longitudinal axis configured to engage bone, a receiving member for receiving a spinal fixation element and for engaging the proximal head of the bone anchor and a restriction member inserted in the receiving member. The restriction member allows the bone anchor to pivot relative to the receiving member about a first axis of the proximal head in at least a first direction and restricts the bone anchor from pivoting about a second axis of the bone anchor in a second direction. The proximal head may be received in a cavity of the receiving portion.

In one embodiment, the first axis is perpendicular to a longitudinal axis of the spinal fixation element. The second axis may be parallel to a longitudinal axis of the spinal fixation element.

The proximal head may have a first curved side surface to facilitate pivoting of the bone anchor in the first direction. In one embodiment, the proximal head includes two opposed side surfaces that are curved. One or more of the curved side surfaces may be curved in three dimensions.

The proximal head may have at least one flat side surface to prevent pivoting of the bone anchor in the second direction.

According to one embodiment, the bone anchor is pivotable in a coronal plane when inserted in a patient. According to one embodiment, the bone anchor is fixed from moving in a sagittal plane when inserted in a patient.

The restriction member in the bone anchor assembly according to the first aspect of the invention may comprise a cap for seating the proximal head within a cavity of the receiving member. In one embodiment, the cap includes a seat for receiving the spinal fixation element. The cap may also include a first protrusion for guiding the movement of the bone anchor, which may be coupled to or integrally formed with the cap. The proximal head may include a projection or other suitable mating means for mating with a recess on the protrusion. A second protrusion may extend from the cap, with each protrusion configured to abut a side surface of the proximal head. One or both of the protrusions may have a flat surface configured to abut a corresponding flat surface of proximal head.

The anchor portion may be restricted to pivoting about a single axis only relative to the rod-receiving portion, or may pivot about multiple axes relative to the rod-receiving portion.

According to another aspect, a bone anchor assembly comprises a bone anchor having a distal shaft extending along a longitudinal axis configured to engage bone and a proximal head having at least one flat side surface extending substantially parallel to the longitudinal axis and a restriction member. The restriction member receives the proximal head on a first side and configured to mate with a first flat side surface of the proximal head to prevent pivoting of the distal shaft about a first axis of the proximal head that is parallel to the first flat side surface.

According to another aspect of the invention, a bone anchor assembly comprises a bone anchor having a distal shaft extending along a longitudinal axis configured to engage bone and a substantially spherical proximal head having at least one flat side surface extending substantially parallel to the longitudinal axis. A receiving member receives a spinal fixation element and movably engages the spherical proximal head. A restriction member is inserted in the receiving member for mating with the flat side surface of the anchor head to prevent rotation of the bone anchor relative to the receiving member in a direction that is perpendicular to the flat side surface.

The restriction member in the bone anchor assembly may comprise a cap disposed over a top surface of the proximal head and a first protrusion extending from the cap over the flat side surface of the proximal head, and the first protrusion may be integrally formed with or coupled to the cap. In one embodiment, the first protrusion has a flat surface configured to abut the flat surface of proximal head. The restricting member may further comprise a second protrusion opposed to the first protrusion for mating with a second flat surface on the proximal head.

According to still another aspect of the invention, a bone anchor assembly comprises a bone anchor having a distal shaft extending along a longitudinal axis configured to engage bone and a proximal head having at least one flat side surface extending substantially parallel to the longitudinal axis and a capping member configured to engage the proximal head on a first side and a spinal rod on a second side, the capping member including a first protrusion extending over and abutting a first flat side surface to prevent rotation of the distal shaft about a first axis of the proximal head that is parallel to the first flat side surface. The capping member may prevent the anchor portion from pivoting out of a plane aligned with the rod. The proximal head may be substantially spherical in shape.

The first flat side surface on the proximal head may include a projection for engaging a recess in the protrusion to mate the first flat side surface to the protrusion.

The capping member may include a rod seat for receiving the rod on the second side. The rod seat may have a longitudinal axis that is perpendicular to the first axis of the proximal head about which the shaft pivots.

According to another aspect of the invention, a bone anchor assembly includes a bone anchor having a distal shaft extending along a longitudinal axis configured to engage bone and a proximal head and a rod seat coupled to the bone anchor for seating a spinal rod. The rod seat allows for a relative pivoting movement between the bone anchor and a spinal rod inserted in the rod seat in at least a first direction, while restricting relative pivoting movement between the bone anchor and the spinal rod in a second direction. The rod seat may pivot relative to the bone anchor to facilitate pivoting of the bone anchor relative to the spinal rod. The bone anchor assembly may further comprise a receiving member coupled to the bone anchor for housing the rod seat. The rod seat may comprise a lower rod seat coupled to the receiving member and having a substantially spherical surface configured to slidably mate with a recess in the proximal head of the bone anchor and an upper rod seat pivotably connected to the receiving member, so that the lower rod seat and upper rod seat define therebetween a movable channel for receiving the spinal rod and for allowing relative movement between the bone anchor and the spinal rod.

BRIEF DESCRIPTION OF THE DRAWINGS

The foregoing and other objects, features and advantages of the invention will be apparent from the following description and apparent from the accompanying drawings, in which like reference characters refer to the same parts throughout the different views. The drawings illustrate principles of the invention and, although not to scale, show relative dimensions.

FIGS. 13A-13C illustrate a constrained motion bone screw according to still another embodiment of the invention.

FIGS. 14A-14B illustrate different views of a rod seat for the constrained motion bone screw of FIGS. 13A-13C.

DETAILED DESCRIPTION OF THE INVENTION

Figure 1:
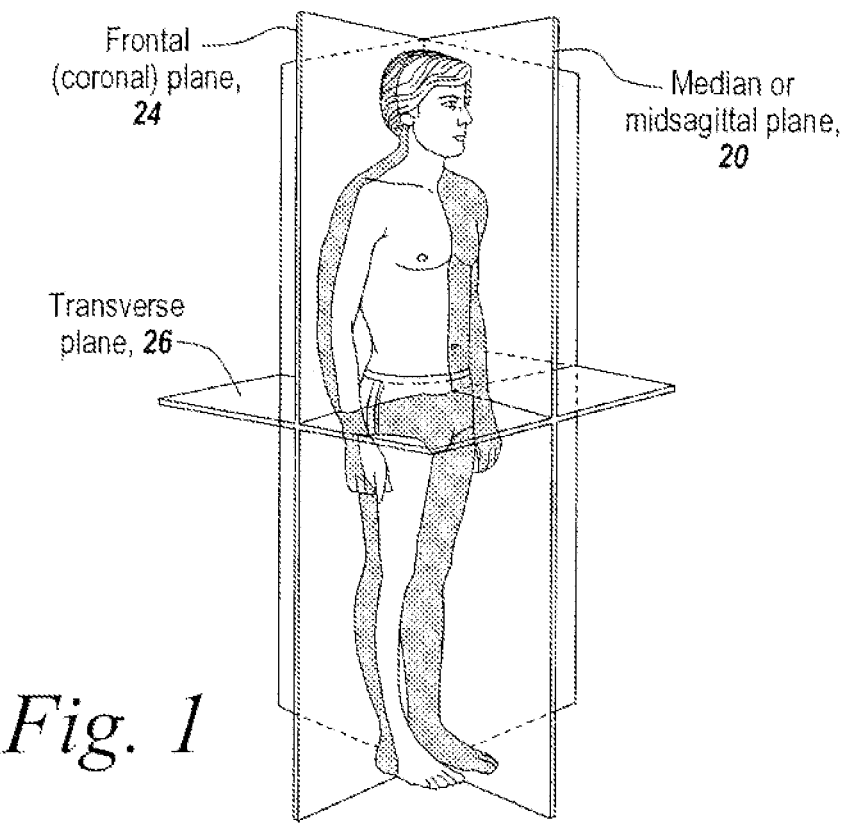
FIG. 1 is a diagram of the human body, illustrating the three planes used to help describe the human anatomy.

The present invention provides an improved bone screw assembly in a spinal fixation system. One skilled in the art will recognize that the invention is not limited to use in bone or in spinal surgery, and that the instrument and methods described herein can be adapted for use with any suitable surgical device to be moved into a selected position in a variety of medical procedures. The present invention will be described below relative to certain exemplary embodiments to provide an overall understanding of the principles of the structure, function, manufacture, and use of the instruments disclosed herein. Those skilled in the art will appreciate that the present invention may be implemented in a number of different applications and embodiments and is not specifically limited in its application to the particular embodiments depicted herein.

During spinal deformity surgeries, it may be necessary to de-rotate the vertebral bodies to normalize the spine. Due to varying patient anatomy, insertion of fixed angle screws, where the anchor portion of the screw extends at a fixed angle relative to the rod-receiving portion of the screw can be difficult. Polyaxial and multi-axial screws, which allow the screw shank to pivot in all directions about the head portion, can be difficult to control and often result in undesirable movement in certain planes. A constrained motion bone screw assembly, different embodiments of which are illustrated in FIGS. 3-13C, allows for angulation of the anchor portion relative to a head portion in at least one plane, such as the coronal plane of the human body, but prevents angulation in another plane, such as the sagittal plane of the human body. For a bone screw assembly used to couple a spinal rod to bone, such as the pedicle bone, to prevent angulation in the sagittal plane, the controlled movement bone screw assembly permits rotation of the anchor portion about an axis perpendicular to a rod coupled to the bone screw assembly, while preventing, blocking, prohibiting or otherwise constraining rotation of the anchor portion about an axis extending parallel to the rod. The controlled movement bone screw assembly of the present invention may allow a surgeon to rotate vertebral bodies and facilitates rod placement into the rod-receiving portion.

The exemplary bone screw assemblies of the illustrative embodiments of the invention may be employed to engage one or more spinal fixation elements to bone. For example, a bone screw assembly may be employed to fix a spinal plate, rod, and/or cable to a vertebra of the spine. Although the exemplary bone screw assemblies described below are designed primarily for use in spinal applications, and specifically the pedicle region of a vertebra, one skilled in the art will appreciate that the structure, features and principles of the exemplary bone screw assemblies, as well as the other exemplary embodiments described below, may be employed to couple any type of orthopedic implant to any type of bone or tissue.

The bone screw assembly described herein facilitates the correction of the position, for example, the angular orientation, of the vertebra in which the bone screw is implanted. For example, the bone screw assembly may be configured to provide stability in one plane, for example, the transverse plane, by restricting pivoting of the receiver member of the bone screw assembly in the selected plane. The stability of the bone screw assembly in the selected plane facilitates movement of the bone screw assembly and associated vertebra in the selected plane. e.g., facilitates rotation of the bone anchor assembly and the vertebra about an axis that intersects the plane. Exemplary instruments and methods for manipulating a bone anchor assembly connected to a vertebra are described in detail in U.S. patent application Ser. No. 11/073,352, filed concurrently herewith, entitled Instruments and Methods for Manipulating a Vertebra, incorporated herein by reference.

FIG. 1 is a diagram of the human body, and illustrates the three planes used to help describe anatomy. As shown in FIG. 1, the sagittal plane 20 splits the body from head to toe, from the back or posterior to the front or anterior. The coronal plane 24 splits the body from head to toe, side to side. The transverse plane 26 slices through the body yielding cross-sectional views. According to one aspect of the invention, a constrained motion bone screw assembly 30, shown in FIG. 2, includes an anchor portion 32 that is controllably pivotable in selected directions about one or more axes passing through a pivot point P with respect to a head portion 34, which may be a receiving portion, such as a rod-receiving portion, for receiving a spinal rod or other spinal fixation element.

Figure 2:
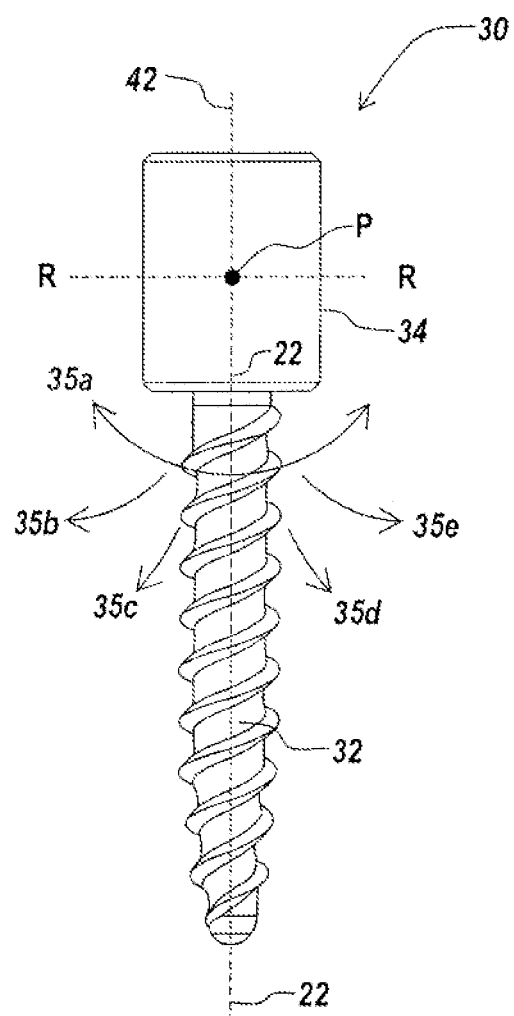
FIG. 2 illustrates a constrained motion bone screw assembly according to an embodiment of the invention.

The constrained motion bone screw assembly 30 of the present invention further selectively constrains the movement of the anchor portion 32 relative to the head portion 34 and/or a spinal fixation element received in the head portion 34 in one or more selected directions. As shown in FIG. 2, the anchor portion 32 relative to the head portion 34 in several directions about pivot point P, as indicated by arrows 35a-35e. The illustrative anchor portion 32 is prevented from pivoting about axis R-R, which extends through the pivot point P in a direction that is perpendicular to the longitudinal axis of 22 of the shaft. The anchor portion 32 is thus restricted from rotating about the head portion 34 in a direction that is perpendicular to the axis R-R. Preferably, the anchor portion 32 may be adjusted such that the longitudinal axis 22 of the bone anchor portion 32 extends at an angle of between 0° and 90° in the selected direction relative to the longitudinal axis 42 of the head portion 34.

In an alternate embodiment, a rod seat within the head portion 34 may be selectively movable to allow for relative movement between a spinal fixation element, such as a spinal rod, received in the head portion 34 and the bone anchor.

Figures 3, 4:
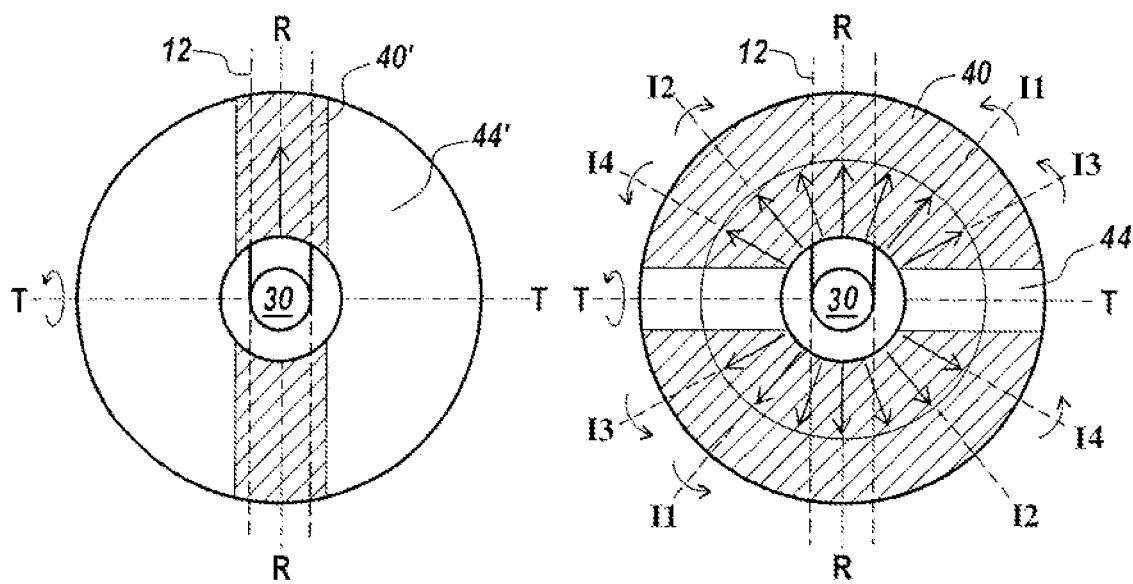
FIG. 3 is a top view illustrating the area in which the anchor portion of the bone screw of FIG. 2 is movable relative to the head portion according to one aspect of the invention.
FIG. 4 is a top view illustrating the area in which the anchor portion of the bone screw of FIG. 2 is movable relative to the head portion according to another aspect of the invention.

FIG. 3 is a top view illustrating the range of motion of the anchor portion 32 relative to the head portion 34 of a bone screw assembly 30 and a rod 12 received by the head portion 34 according to one embodiment of the invention. As shown in FIG. 3, the path of the anchor portion in the region surrounding the head portion may be limited in the sagittal plane, but movable in all other planes around the head portion, including the coronal plane. In FIG. 3, the anchor portion is pivotable not only about axis T-T, which is perpendicular to the longitudinal axis of the rod 12 received by the head portion 34, but also around several intermediate axes I1-I4 extending between the perpendicular axis T-T and the axis R-R to allow movement in the shaded region 40 surrounding the head portion 34. The anchor portion 32 is fixed from rotating about axis R-R, to prevent movement of the anchor portion in perpendicular region 44 extending perpendicular to the longitudinal axis 42 of the head portion.

As shown in FIG. 4, according to another embodiment of the invention, the anchor portion 32 may be fixed in all planes except for one selected plane, such as the coronal plane, to allow for movement of the anchor portion along a selected path in a single plane, such as the sagittal plane, while preventing movement of the anchor portion out of the single plane in all other directions relative to the head portion. In the embodiment of FIG. 4, the anchor portion is only pivotable about axis T-T, so that the range of motion of the anchor portion relative to the head portion is limited to the region 40' that is parallel to and aligned with the rod 12. Because the anchor cannot pivot about other axes, the anchor portion cannot move into the region 44' and is fixed in the plane defined by region 40'. The region 40' may encompass the sagittal plane when the screw assembly is inserted in a patient. One skilled in the art will recognize that ranges of motion between those illustrated in FIGS. 3 and 4 are also contemplated by the present invention.

Figure 5:
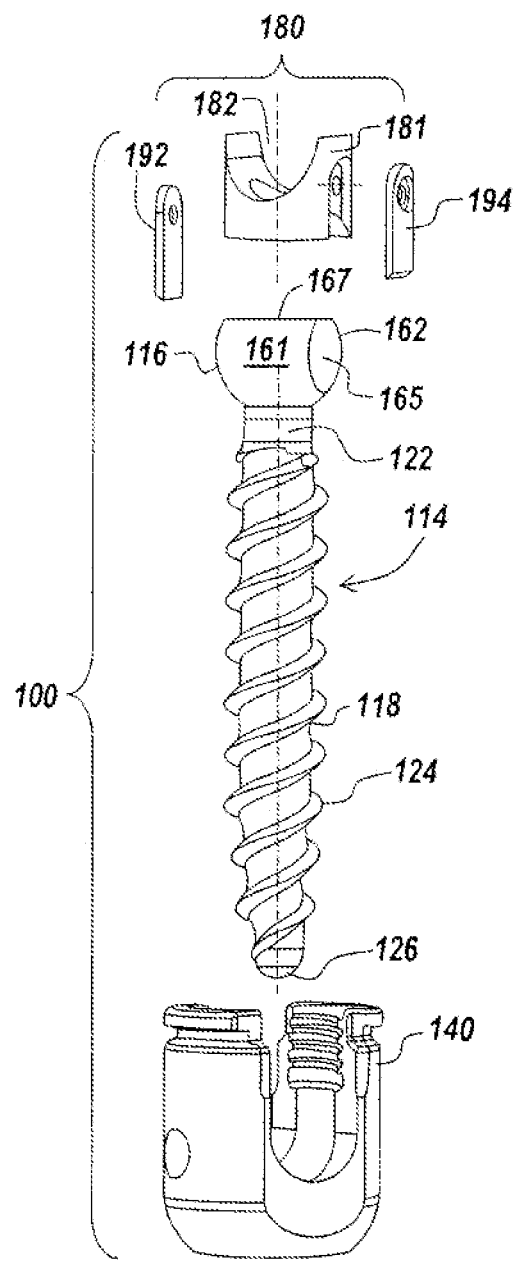
FIG. 5 illustrates an embodiment of a constrained motion bone screw according to an illustrative embodiment of the invention.
Figure 6:
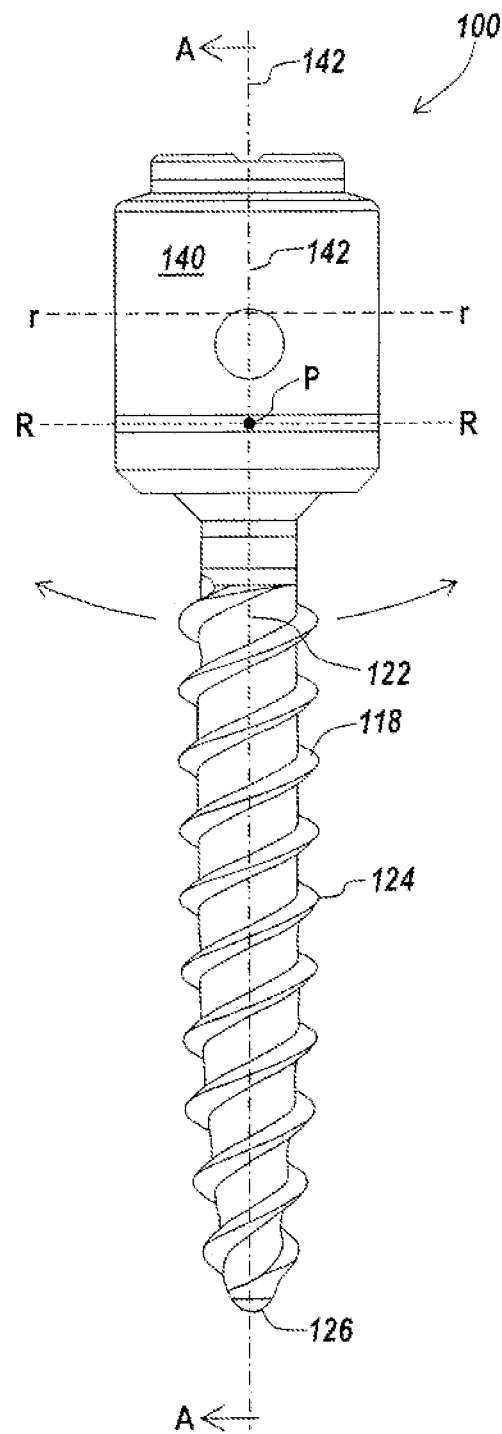
FIG. 6 is a side view of the assembled bone screw of FIG. 5.
Figure 7:
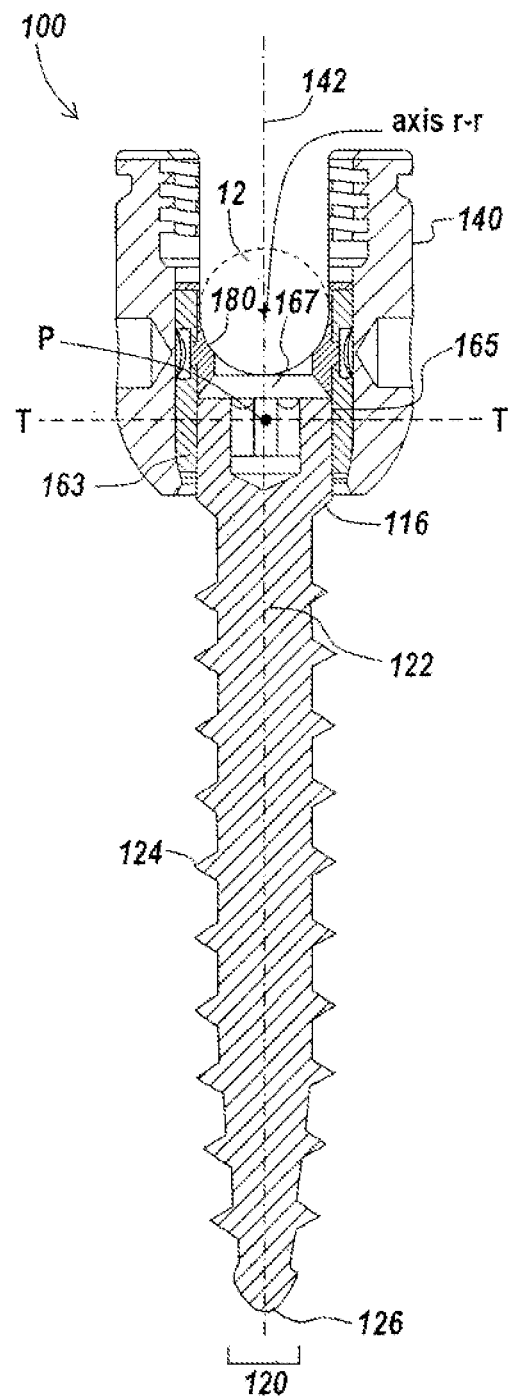
FIG. 7 is a cross-sectional view along axis A-A of FIG. 6.

FIG. 5 is an exploded view of an embodiment of a bone screw assembly 100 including a bone anchor portion 114, illustrated as a threaded shaft, coupled to a head portion, illustrated as a rod-receiving portion 140, to allow for controlled movement between the bone anchor 114 and rod-receiving portion 140 in accordance with the teachings of the invention. A compression and restriction member 180 for seating the head of the anchor portion 114 within the rod-receiving portion 140 includes restricting protrusions or other suitable mechanisms for selectively limiting the movement of the bone anchor relative to the rod-receiving portion to one or more selected directions. FIG. 6 is a side view of the assembled bone screw assembly 100. FIG. 7 is a cross-sectional view of the assembled bone screw assembly 100 along axis A-A shown in FIG. 6.

The bone anchor 114 comprises a joint portion, illustrated as a proximal anchor head 116, for coupling the bone anchor 114 to the rod-receiving portion 140, and an anchoring portion, illustrated as a distal shaft 118 configured to engage bone. The distal shaft 118 of the bone anchor 114 has a shaft diameter 120 and a longitudinal axis 122. The distal shaft 118 may include one or more bone engagement mechanisms to facilitate gripping engagement of the bone anchor to bone. In the illustrated embodiment, the distal shaft 118 includes an external thread 124 extending along at least a portion of the shaft for engaging bone. In the illustrated embodiment, the external thread 124 is a single lead thread that extends from a distal tip 126 of the shaft to the anchor head 116, though one skilled in the art will recognize that the external thread may extend along any selected portion of the shaft and have any suitable number of leads. Other suitable bone engagement mechanisms include, but are not limited to, one or more annular ridges, multiple threads, dual lead threads, variable pitched threads and/or any conventional bone engagement mechanism.

The rod-receiving member 140 receives the proximal head 116 of the bone anchor to couple the bone anchor 114 thereto, thereby coupling the bone to a rod or other element received in the rod-receiving member 140. The illustrative rod-receiving member 140 may be substantially similar to a head portion of a polyaxial screw assembly of the prior art. In a rest position, the longitudinal axis 122 of the bone anchor aligns with a longitudinal axis 142 extending through the rod-receiving member 140. The distal shaft 118 is pivotable relative to the rod-receiving member 140 about the proximal head 116 in one or more selected directions to angulate the longitudinal axis 122 relative to the longitudinal axis 142. The screw assembly 100 further includes one or more components, illustrated as the compression and restriction member 180, for preventing a pivoting movement of the distal shaft 118 in one or more directions, so that the distal shaft 118 cannot pivot in all 360 degrees around the rod-receiving member 140, thereby increasing the stability of the screw assembly in one or more planes, as described in detail below. For example, referring to FIGS. 6 and 7, the shaft is pivotable about axis T-T, but constrained from pivoting about axis R-R. Axis R-R is aligned with and parallel to the longitudinal axis r-r of the rod 12 in a selected plane and perpendicular to axis T-T, intersecting T-T at pivot point P, and may be substantially parallel to the longitudinal axis r-r of a rod to be received in the receiving portion 140.

The anchor head 116 of the bone anchor 114 may be configured to facilitate controlled adjustment of the bone anchor 114 relative to the receiving member 140 of the bone screw assembly. For example, the illustrative anchor head 116 may be substantially spherical and include curved side surfaces 161, 162 that are shaped to permit pivoting of the bone anchor 114 relative to the receiving member 140 in one or more selected directions. The curved side surfaces 161, 162 are preferably curved in three-dimensions to facilitate rotation of the anchor portion 114 relative to the receiving member 140. The illustrative anchor head 116 further includes two opposed flat side surfaces 163, 165 for constraining the pivoting movement to the one or more selected directions. The flat surfaces 163, 165 preferably extend substantially parallel to the longitudinal axis 122 of the shaft 118. While the illustrative embodiment shows two opposed flat side surfaces 163, 165, one skilled in the art will recognize that the head can have any suitable number of flat surfaces or other selected feature for limiting the path of the shaft 118 relative to the receiving portion 140 about any selected axis or axes. The top surface 167 of the anchor head 116 may be a generally planar surface to facilitate seating of the anchor within the rod-receiving portion 140 of the screw assembly. The anchor head 116 may also have surface texturing, knurling and/or ridges.

Figures 8A, 8B, 8C:
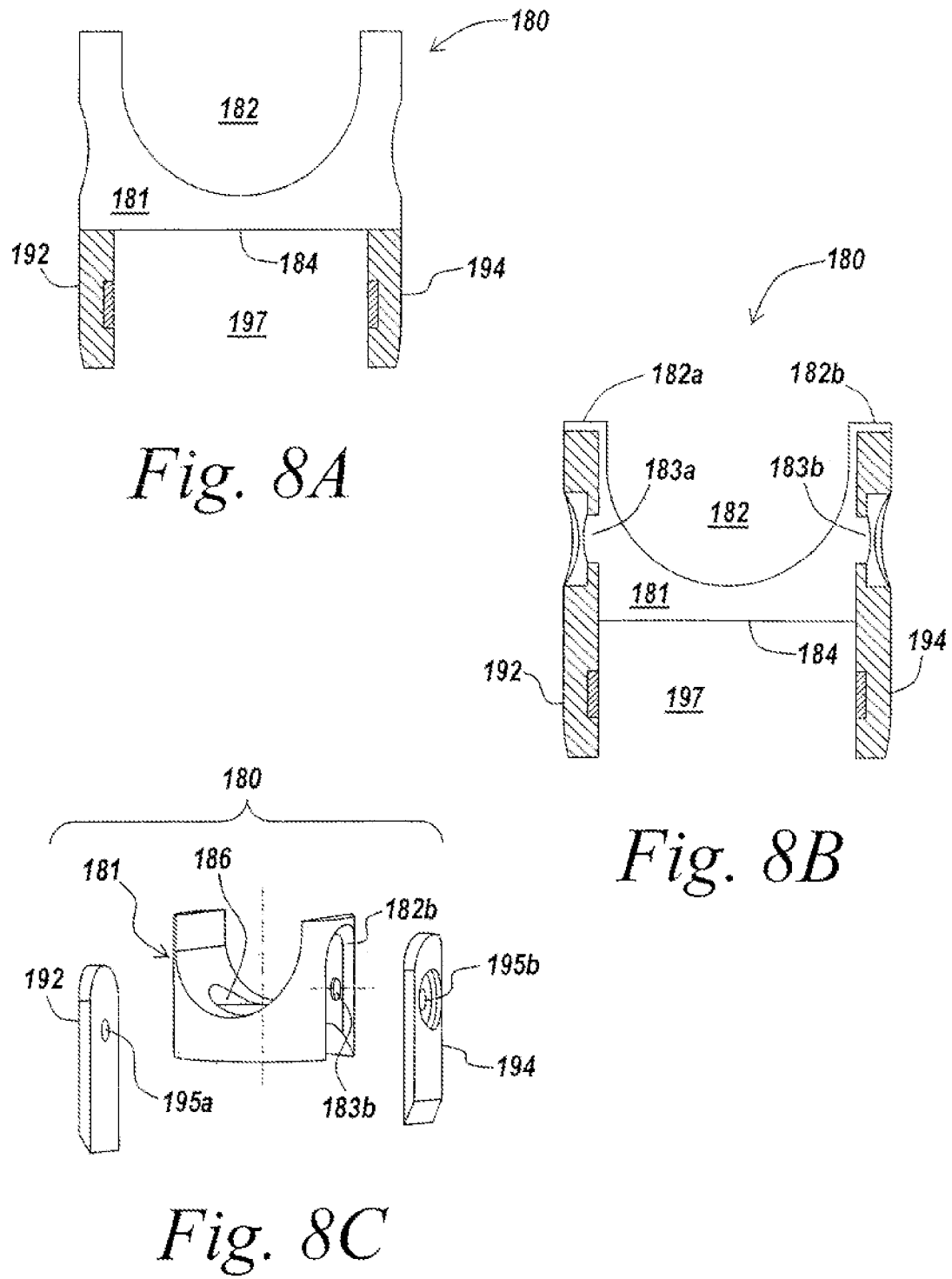
FIG. 8A-8C illustrate in detail the compression and restriction member of the bone screw assembly of FIG. 5.

The illustrative bone screw assembly 100 further includes a compression and restriction member 180 for seating the anchor head 116 within the rod-receiving portion 140 of the screw 100 and for cooperating with the flat surfaces 163, 165 to constrain the movement of the anchor portion relative to the rod-receiving portion 140 and/or a rod received therein. The compression and restriction member 180 preferably forms a proximal rod seat 182 for seating a rod or other spinal fixation element and an opposed distal anchor seat 197 for engaging the anchor head 116. FIGS. 8A-8C illustrate an embodiment of the compression and restriction member 180 in detail, though one skilled in the art will recognize that the invention is not limited to the illustrative embodiment. The illustrative compression and restriction member 180 includes a cap 181 and restricting protrusions 192, 194 that extend from a lower surface 184 of the cap 181. The restricting protrusions 192, 194 form a track-like region 197 for receiving the anchor head 116 therebetween. The restricting protrusions 192, 194 are configured to mate with the flat surfaces 163, 165 of the anchor head 116 when the bone screw assembly 100 is assembled to guide and constrain the pivoting movement of the anchor head 116 relative to the receiving member 140. The illustrative restricting protrusions 192, 194 restrict movement of the anchor head 116 about axis T-T through a plane that is parallel to the flat faces 163, 165 of the proximal head 116 and the protrusions 192, 194.

In illustrative embodiment of FIGS. 5-SC, the plane through which the anchor portion 114 pivots is preferably defined by the longitudinal axis r-r of a rod inserted in the rod-receiving member 140 when the screw assembly 100 is assembled and the longitudinal axis 142 of the receiving member 140, similar to the assembly of FIG. 4B. However, one skilled in the art will recognize that the screw assembly 100 of FIGS. 5-8C may also be made to pivot in one or more other directions relative to the rod-receiving member 140.

In the embodiment shown in FIGS. 8A-8C, the restricting protrusions 192, 194 comprise separate inserts that couple to the cap 181. For example, the illustrative cap 181 includes side recesses 182a, 182b, each sized and configured to receive a top end of a restricting protrusion 192, 194, respectively. Each recess may further include a coupling projection 183a, 183b configured to mate with a hole or recess 195a, 195b, in an associated restricting projection 192, 194, respectively, to facilitate coupling of the restricting projection to the cap. When coupled, each restricting projection extends past the bottom surface 184 of the cap 181 to cover and abut the flat surfaces 163, 165 of the anchor head 116 when the screw is assembled to control the movement of the anchor 114 relative to the rod-receiving member 140.

One skilled in the art will recognize that any suitable means for coupling the restricting protrusions to the cap 181 may be used. Alternatively, one or more of the restricting protrusions 192 or 194 may be integrally formed with the cap 181.

The restriction and compression member 180 is positioned within the receiving member 140 between the spinal rod 12 and the anchor head 116 when the bone screw assembly is assembled. The restriction and compression member 180 preferably engages the spinal rod 12 and the anchor head 116 to facilitate assembly of the constrained motion bone screw assembly 100.

According to another embodiment of the invention, a restriction member is provided for restricting pivoting of the bone anchor relative to the receiving member that does not necessarily serve as a compression member and/or a rod seat for seating the spinal rod or other spinal fixation element coupled to the bone anchor assembly.

Figure 9C:
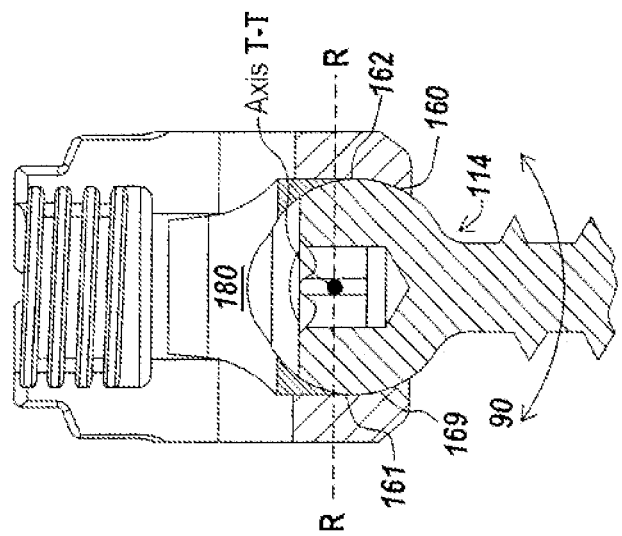
FIG. 9A-9C are detailed views of the constrained motion bone screw assembly of FIG. 5 in the vicinity of the receiving member.
Figure 9B:
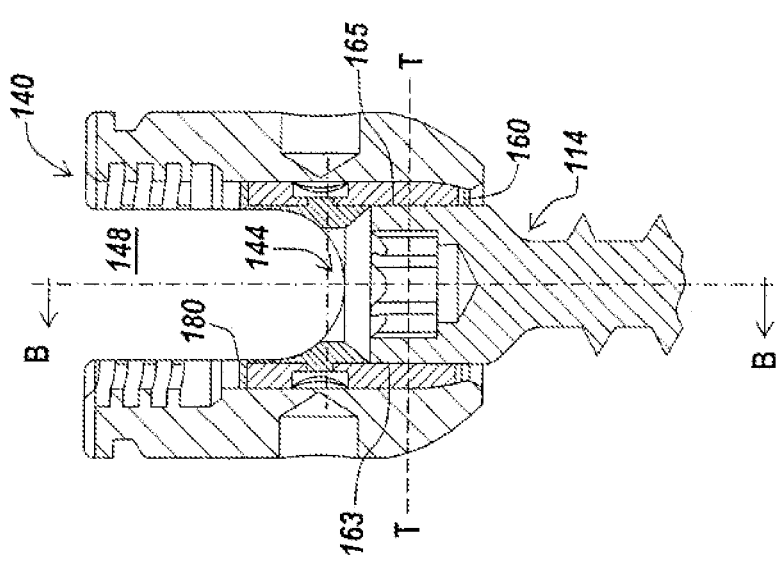
Figure 9A:
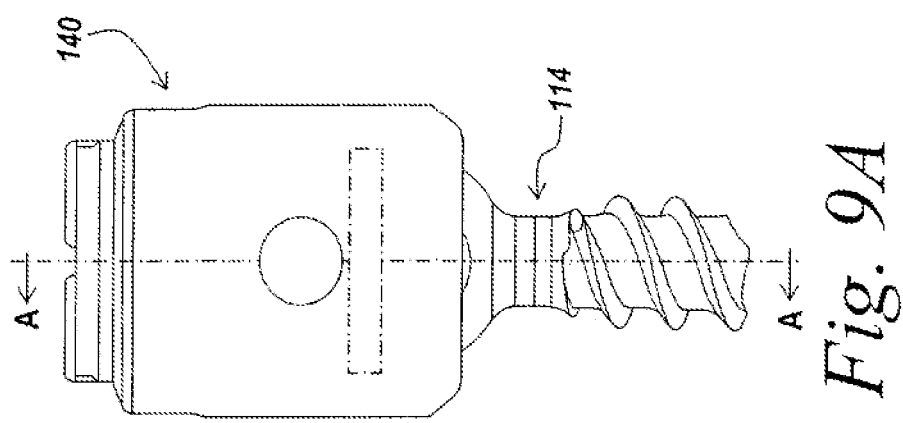

FIGS. 9A-9C are detailed views of the illustrative rod-receiving member 140 when assembled. As shown in FIG. 9B, the flat surfaces 163, 165 of the proximal head interact with the flat surfaces of the protrusions 192, 195 to prevent movement or rotation of the shaft 118 against the flat surfaces. As shown in FIG. 9C, the curved side surfaces 161, 162 of the proximal head 116 allow for rotation of the bone anchor 114 relative to the rod-receiving member 140 in the direction indicated by arrow 90 about axis T-T.

In the illustrative embodiment, the restricting protrusions 192, 194 restrict the movement of the anchor shaft along a predetermined axis through an interference fit between the flat surfaces 163, 165 of the anchor head 116 and the restricting protrusions 192, 194. However, one skilled in the art will recognize that any suitable means may be used to restrict the movement of the shaft to one or more selected directions.

Figure 10:
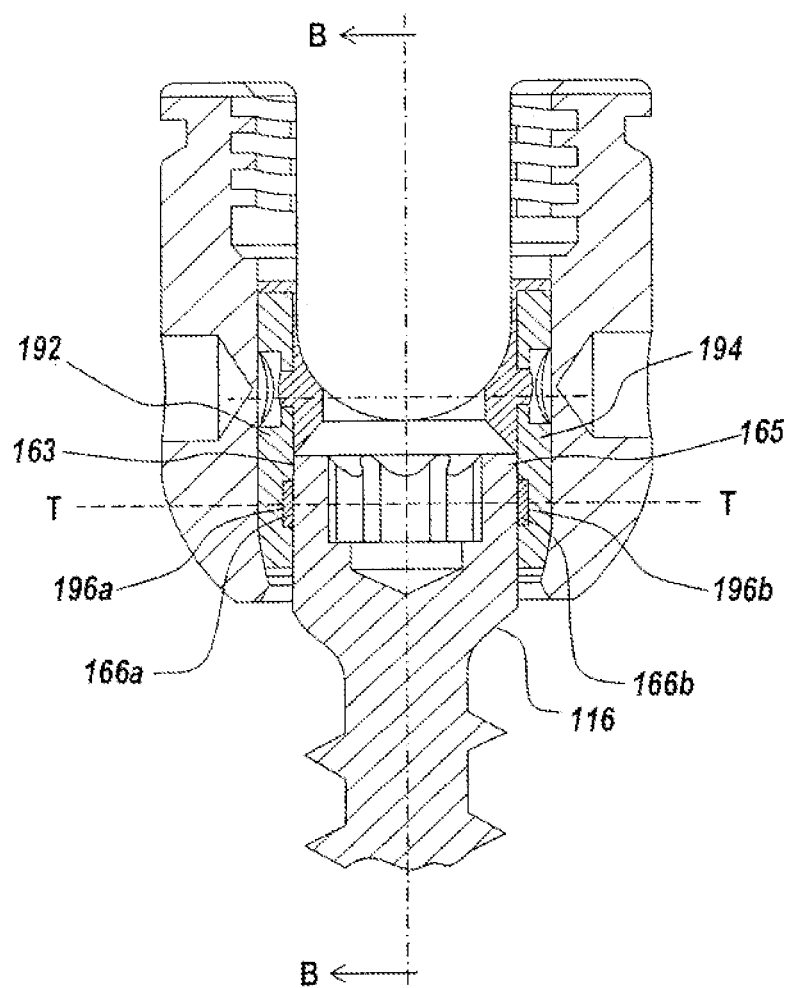
FIG. 10 illustrates a constrained motion bone screw according to another embodiment of the invention.

The invention is not limited to the illustrated mechanism for constraining the motion of the shaft relative to the rod-receiving portion. For example, as shown in FIG. 10, the anchor head 116 may include projections 166a, 166b extending from the side surfaces 163, 165, respectively that are configured to interface with recesses 196a, 196b in the restricting protrusions 192, 194 of the illustrative compression and restriction member to form a fixed pivot point about which the anchor 114 can rotate. Alternatively, the restricting protrusions may include projections configured to be received in the recesses formed in the side surfaces 163, 165 to facilitate coupling of a compression and restriction member to the proximal head that selectively limits rotation of the anchor in one or more directions while facilitating rotation in one or more other directions.

In addition, while the illustrative protrusions include flat surfaces configured to abut flat surfaces on the proximal head 116 to restrict rotation along a single axis, the restricting protrusions can alternatively be designed to allow for rotation about one or more of the intermediate axes I1-I4 shown in FIG. 3.

According to an illustrative embodiment of the invention, the receiving member 140 of the constrained motion bone screw assembly defines a recess 148. The recess 148 may be sized and shaped to receive a spinal rod 12 that extends along axis r-r or another suitable spinal fixation element. The exemplary spinal rod 12 may be seated within the recess 148 by aligning the spinal rod 12 and the recess 148 and advancing the spinal rod through a top bore hole into the recess 148. The configuration of the recess 148 may be varied to accommodate any suitable spinal fixation element. A suitable configuration for the receiving member 140 is described in the U.S. Patent Application Publication Numbers US 2004/0186473, US 2004/0181224 and US 2003/0100896, the contents of which are herein incorporated by reference.

In other embodiments, a spinal fixation element may be coupled to the bone anchor by alternative coupling mechanisms in place of a recess, including, for example, an offset coupling mechanism, such as a band clamp, sacral extender, or a lateral off-set connector.

The receiving member 140 may couple the spinal fixation element seated therein to the bone anchor 116 through any suitable means. For example, in the illustrative embodiment, the distal end of the receiving member includes an opening 160 through which at least a portion of the bone anchor 114 may extend. The distal opening is preferably smaller in size and shape than the anchor bead 116 so as to engage the head 116 of the bone anchor 114. The distal opening 160 may define a seat 169 to allow the bone anchor 114 to selectively pivot relative to the receiving member. The screw is assembled by inserting the shaft through the first opening 160 until the head 116 is received in and constrained by the cavity 169.

The illustrative compression and restriction member cap 181 may be generally disc-shaped having a circular cross-section or other cross section preferably corresponding to a first bore 144 of the receiving member 140. A first surface of the compression and restriction member 180 may be configured to seat the spinal fixation element. In the illustrative embodiment, the seat 182 formed in the first surface has a generally arcuate cross-section having a curvature that may approximate the curvature of the exemplary spinal rod to be received therein. The second surface 184 may be configured to engage the anchor head 116. For example the second surface 184 may have a generally concave spherical shape or a tapered shape to engage the head of the bone anchor. The illustrative second surface 184 has a hemispherical shape to approximate the curvature of the anchor head 116. A bore 186 may extend through the cap 181 to allow for advancement of an instrument to the bone anchor 116 during assembly of the bone screw assembly.

After pivoting the bone anchor portion 116 about a selected axis in a selected direction relative to the receiving portion 140 by a selected degree, preferably between 0° and 90°, a user can lock the orientation of the anchor portion relative to the rod-receiving portion by inserting a closure mechanism, such as a set screw. The closure mechanism secures a spinal rod 12 or other suitably configured spinal fixation element within the recess 148 of the receiving member 140 and locks the anchor head 116 in the selected orientation within and relative to the receiving member 140. In the illustrative embodiment, distal advancement of the closure mechanism into engagement with the spinal rod 12 in the recess 148 seats the spinal rod in the seat 182 of the compression and restriction member 180. The compression and restriction member 180 or other suitable restriction member may compress against the anchor head 116 to lock anchor in the selected orientation. Other suitable closure mechanisms may be employed to secure the spinal fixation element to the assembly and/or to lock the orientation of the bone anchor relative to the receiving portion.

While the illustrative restricting protrusions 192, 194 restrict pivoting of the anchor in a single direction about a single axis, one skilled in the art will recognize that the invention is not limited to restricting movement to a single direction about a single axis. As described above, the compression and restricting member 180 or other suitable restriction member may also be configured to allow some rotation of the anchor portion about the longitudinal axis 122, or allow pivoting in an intermediate direction about an intermediate axis I-I between axes T-T and R-R, while restricting the anchor from being able to move in any direction in the full 360 degree around the rod-receiving member 140, as shown in FIG. 3.

The receiving member 140, in certain exemplary embodiments, may be configured to receive a spinal fixation element, such as a rod, and couple the spinal fixation element to the bone screw assembly 100. As shown, the recess 148 is sized and shaped to receive a spinal rod, though one skilled in the art will recognize that the receiving member 140 may be configured to accommodate any suitable spinal fixation element.

Figure 11:
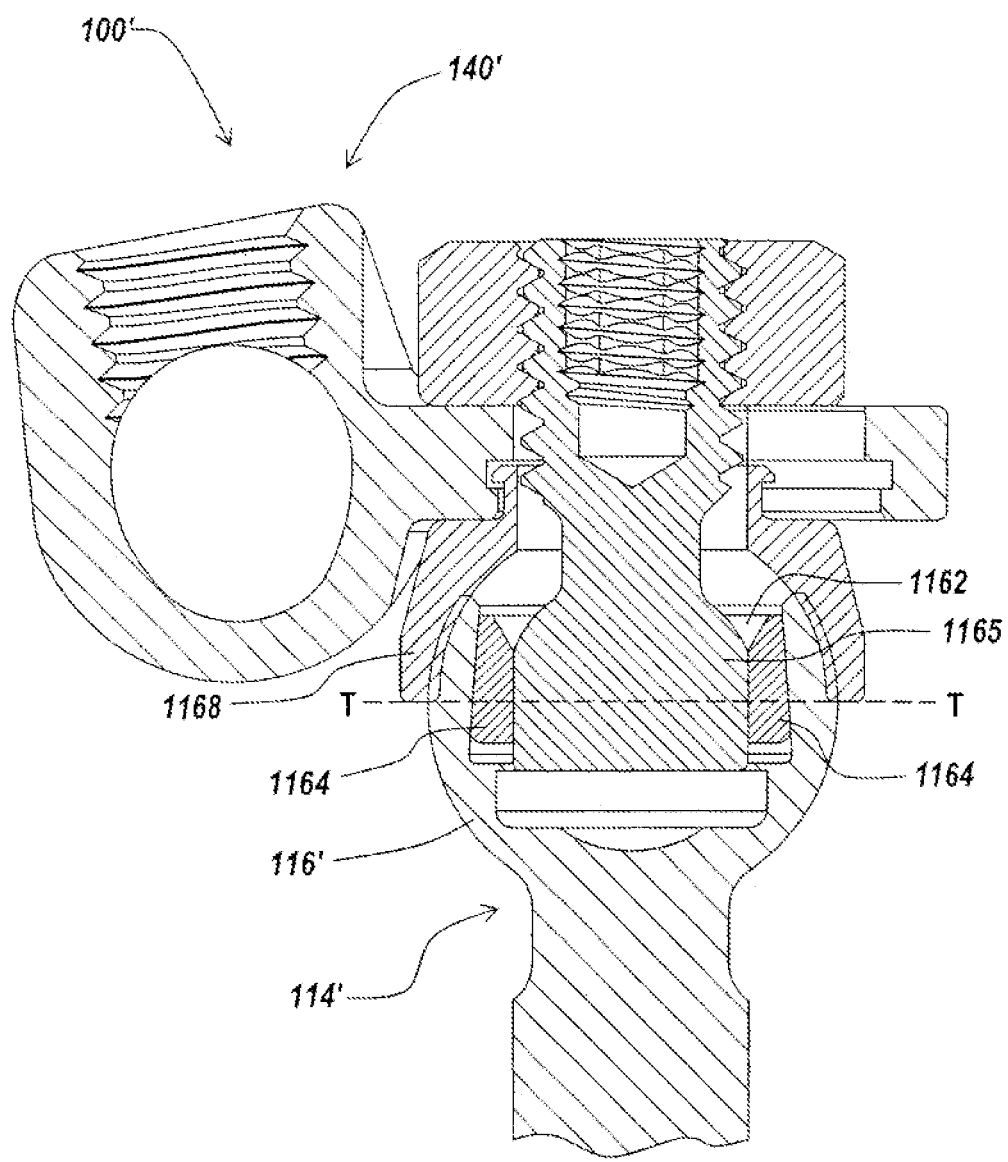
FIG. 11 illustrates a constrained motion bone screw according to another embodiment of the invention.

In another embodiment of the invention, shown in FIG. 11, the proximal head 116' of the anchor portion 114' of a constrained motion bone screw assembly 100' is substantially spherical and curved on all side surfaces. The proximal head 116 includes a cavity 1162 formed in the top surface for receiving a ball end 1165 of a receiving member 140'. A retention ring 1164 inserted in the cavity 1162 secures the ball end 1165 within the cavity to couple the anchor portion 114' to the receiving member 140'. A support collar 1168 extends from the receiving member 140 over a portion of the proximal head 116' to maintain the position of the anchor portion and the receiving member. The ball end 1165 of the receiving member may include one or more flat surfaces that abut flat surfaces on the retention ring 1164 to constrict rotation of the anchor portion relative to the ball end in one or more selected directions.

Alternatively, the collar portion 1168 and the outer surface of the substantially spherical proximal head 116' may be configured so as to selectively prohibit rotation of the anchor portion relative to the receiving member in one or more selected directions while allowing rotation in one or more different directions.

Other details of the bottom-loading screw assembly shown in FIG. 11 are described in U.S. Pat. No. 6,623,485 which is incorporated herein by reference.

While the illustrative embodiment is a top-loading screw, one skilled in the art will recognize that the present invention encompasses a bottom-loading screw as well. For example, the first opening 160 of the receiving member may be larger than the head 116 to allow the head to pass through the opening 160 during assembly of the screw. The anchor head would then be inserted through a bottom opening of the receiving member and retained therein by a securing means, i.e., the anchor head is smaller in diameter than the bottom opening of the receiving member. In contrast, the anchor head of a top-loading screw is smaller than the bottom opening of the receiving member. A top-loading screw is assembled by inserting the shaft through the bottom opening, so that the anchor head is retained within a cavity in the receiving member. A bottom-loading screw is assembled by inserting the anchor head through the bottom opening, and inserting and activating the securing means to prevent the anchor head from passing through the opening.

Figure 12:
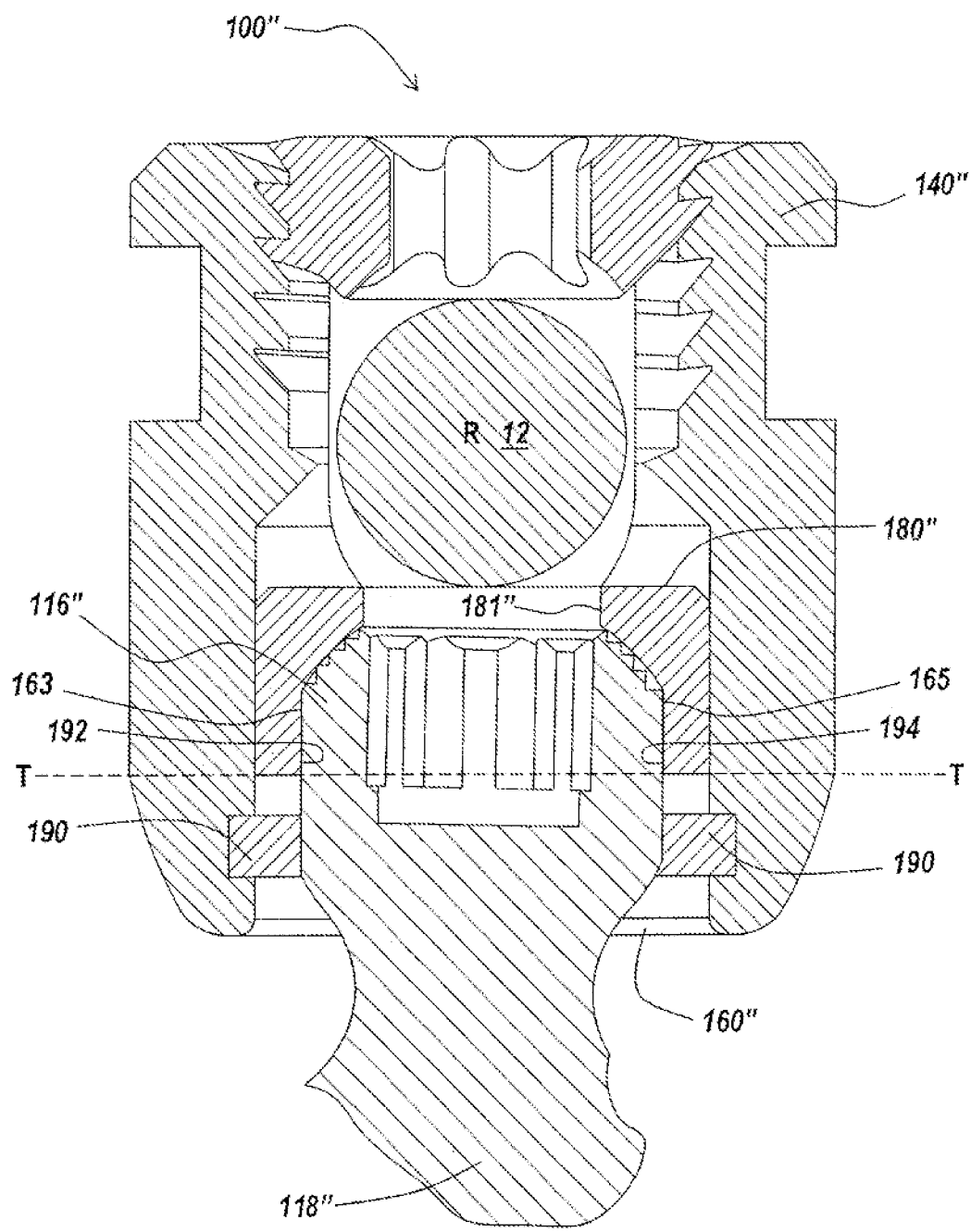
FIG. 12 illustrates a constrained motion bone screw according to another embodiment of the invention.

FIG. 12 illustrates an embodiment of a bottom-loading constrained motion bone screw assembly 100" according to an alternate embodiment of the invention. As shown, the receiving member 140" is configured to receive a rod 12 and has a bottom opening 160" sized and configured to allow insertion of the anchor head 116" therethrough. A retaining member 190 is provided for retaining the anchor head 116" within the receiving member 140". The illustrative retaining member 190 is disposed around the bone anchor and in a groove of the receiver member 140" to lock the anchor head 116" within the cavity of the receiving member. As shown, a compression and restriction member 180" comprises a capping member 181". The capping member is shaped to accommodate the anchor head 116". According to the illustrative embodiment, the capping member 181" includes flat surfaces 192", 194", that are parallel to the longitudinal axis of the anchor shaft 118". The anchor head 116" includes flat surfaces 163", 165" configured to mate with the flat surfaces 192", 194" of the compression and restriction member 180" to prevent rotation of the anchor about an axis that extends through the middle of the anchor head 116" substantially parallel to the axis of the rod, i.e., the anchor cannot move in a direction transverse to the flat surfaces 163" 165". However, the spherical shape of the side surfaces of the anchor head adjacent to the flat surfaces allows for rotation of the anchor about the axis T-T. After angulation of the anchor about the axis T-T by a selected amount, a closure mechanism may be inserted to lock the rod in the receiving member and/or lock the orientation of the anchor. Preferably, the closure mechanism presses down on the compression and restriction member 180" and locks the bone anchor between the compression and restriction member 180" and the retaining member 190.

Other details of the bottom-loading screw assembly 100" shown in FIG. 12 are described in U.S. Pat. No. 6,280,442, which is incorporated herein by reference.

Figure 13A:
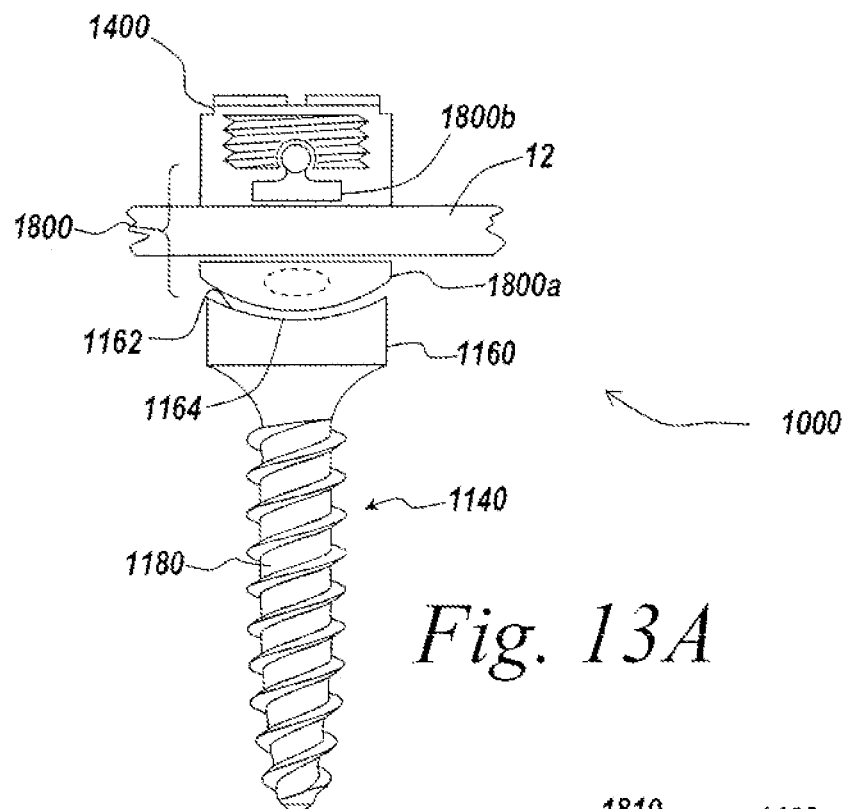
Figure 13B:
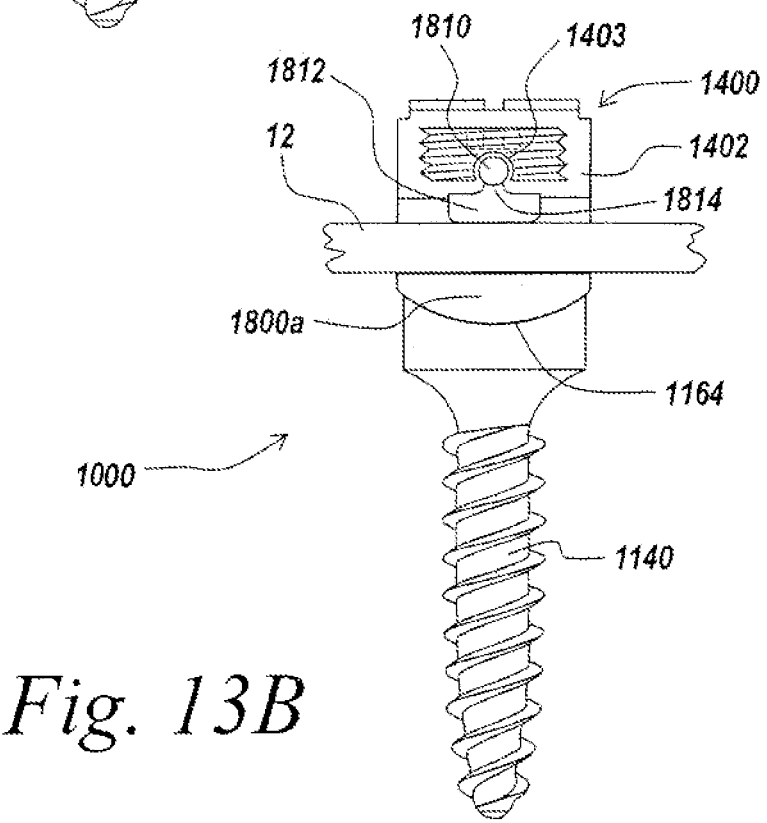

FIGS. 13A-C illustrate another embodiment of a constrained motion bone screw assembly 1000 according to an alternate embodiment of the invention. The constrained motion bone screw assembly 1000 of FIGS. 13A-13C allows for pivoting of a spinal rod received in the constrained motion bone screw assembly 1000 in at least one direction relative to the bone screw assembly 1000, while movement in other directions is restricted. The illustrative constrained motion bone screw assembly 1000 includes a bone anchor portion 1140, a rod-receiving portion 1400 and a movable rod seat 1800 housed by the rod-receiving portion 1400. The illustrative rod seat 1800 includes a lower rod seat 1800a and an upper rod seat 1800b. The lower rod seat 1800a and the upper rod seat 1800b cooperate to define the rod seat 1800 for receiving the rod therebetween. The rod seat 1800 is configured to move in one or more selected directions relative to the bone anchor portion 1140 and the rod-receiving portion 1400 to guide movement of the spinal rod 12 relative to the bone screw assembly 1000. In this manner, both the bone anchor portion 1140 and the rod-receiving portion can move relative to the spinal rod.

As shown, the bone anchor portion 1140 includes a shaft 1180 and a joint portion 1160. The joint portion 1160 includes a recess 1162 formed in a top surface thereof for receiving the lower rod seat 1800a. The recess 1162 preferably has a concave, spherical shape to allow pivoting of the lower rod seat 1800a within the recess 1162.

The illustrative lower rod seat 1800a, shown in detail in FIGS. 14A-14B, is substantially rectangular, with a spherical bottom surface 1802 configured to mate with a concave surface 1164 of the recess 1162. The lower rod seat 1800a includes a flat top surface 1804 for seating the rod 12. The lower rod seat 1800a may include retention recesses 1807a, 1807b on opposing side surfaces 1805, 1806, respectively, for receiving corresponding protrusions (not shown) on the rod-receiving portion 1400 to thereby couple the rod-receiving portion to the lower rod seat 1800a, while allowing selective relative movement between the rod seat and other components of the bone screw assembly 1000.

The rod receiving portion 1400 includes a body 1402, which may comprise one or more components coupled together, and the upper rod seat 1800b pivotably mounted to the body 1402. The upper rod seat 1800b includes a pivot point 1810 received in a recess 1403 of the body 1402 and a rod seat member 1812 connected to the pivot point 1810 via a connecting member 1814. The recess 1403 and pivot point 1810 cooperate to allow for pivoting of the upper rod seat 1800b in one or more selected directions only, while restricting pivoting in other directions.

As shown in FIG. 13C, the illustrative constrained motion bone screw assembly 1000 allows for pivoting of the rod seat 1800 relative to the bone anchor portion 1140 and/or the rod-receiving portion 1400. The selective pivoting of the rod seat 1800 in one or more selected directions to allow bending of the spinal rod 12 received therein relative to the bone anchor portion 1140 and the rod-receiving portion 1400. The lower rod seat and upper rod seat defining therebetween a movable channel for receiving the spinal rod 12 and for allowing for relative movement between the bone anchor portion 1140 and the spinal rod 12, as well as between the rod-receiving portion 1400 and the spinal rod 12. The upper rod seat 1800b pivots in a selected direction, and the lower rod seat 1800a rotates in the recess 1162 to guide the rod's movement, while retaining the rod therebetween. The coupling between the lower rod seat 1800a and the rod-receiving portion 1140 prevent movement in other directions. In this manner, the relative angle between the rod and both the bone anchor portion 1140 and the rod-receiving portion 1400 can be selectively varied in a first direction, while movement in other directions is prevented.

The components of the constrained motion bone anchor assembly of the illustrative embodiments of the invention may be manufactured from any suitable biocompatible material, including, but not limited to, metals and metal alloys such as titanium and stainless steel, polymers and/or ceramics. The components may be manufactured from the same or different materials though manufacturing processes known in the art.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

The invention claimed is:

1. A spinal system, comprising:
   at least a first bone anchor having a proximal head and a distal shaft configured to engage bone, the proximal head having a spherical shape with opposed first and second non-spherical side portions;
   at least a first receiving member being configured to receive the first bone anchor and having a proximal end and a distal end, the proximal end of the first receiving member having two spaced apart upright arms defining a recess for receiving a spinal rod therebetween, the distal end of the at least a first receiving member having a bore therethrough; and
   at least a first cap being configured to be seated within the first receiving member and having a proximal portion configured to seat the spinal rod, the at least a first cap configured to extend around opposed sides of the spinal rod and above a center thereof, the at least a first cap having a cavity formed in a distal portion thereof configured to at least partially receive the proximal head of the first bone anchor,
   first and second restrictor elements each having a first end configured to be removably attached to the at least a first cap and a second end that extends distally beyond the at least a first cap, and that are complementary to and configured to receive the first and second non-spherical side portions of the at least a first bone anchor;
   wherein when the first bone anchor is received in the cavity of the at least a first cap, the first and second restrictor elements engage with at least a portion of the first and second non-spherical side portions of the proximal head to restrict movement of the first bone anchor relative to the at least a first cap in a direction toward and away from the side portions of the at least a first cap.

2. The spinal system of claim 1, wherein at least a portion of each of the first and second restrictor elements are tapered.

3. The spinal system of claim 1, wherein at least a portion of each of the first and second non-spherical side portions of the proximal head of the first bone anchor are opposed flat surfaces.

4. The spinal system of claim 3, wherein the first and second restrictor elements are configured to prevent the first bone anchor from rotating about an axis extending along the distal shaft of the first bone anchor.

5. The spinal system of claim 3, wherein first and second inner surfaces of the first and second restrictor elements are engageable with at least a portion of the first and second non-spherical side portions of the proximal head of the at least a first bone anchor such that the distal shaft of the bone anchor is prevented from moving about an axis that is aligned with and parallel to a longitudinal axis of a spinal rod seated within the first receiving member.

6. The spinal system of claim 1, wherein a first portion of each of the first and second non-spherical side portions of the proximal head of the first bone anchor are opposed flat surfaces, and the cavity of the at least a first cap has a tapered shape to engage the opposed flat surfaces.

7. The spinal system of claim 1, further comprising a second bone anchor having a proximal head and a distal shaft corresponding to the at least a first anchor and a second cap corresponding to the at least a first cap.

8. The spinal system of claim 1, wherein the at least a first cap has a proximal portion with a U-shaped profile.

9. The spinal system of claim 1, further comprising a first closure mechanism being configured to engage with inner surfaces of the arms of the first receiving member to secure the spinal rod within the recess thereof.

10. A spinal system, comprising:
a plurality of bone anchors, each of the plurality of bone anchors having a distal shaft configured to engage bone and a proximal portion engageable with a spinal rod, at least one of the plurality of bone anchors having a restrictive proximal head having a generally spherical outer surface with two opposed restrictive side portions interrupting the generally spherical outer surface;
at least one restrictive cap having a proximal portion configured to receive the spinal rod therein, the at least one restrictive cap having first and second grooves in an exterior thereof, and
first and second protrusions extending distally from the first and second grooves of the restrictive cap, the first and second protrusions being configured to receive the two opposed restrictive side portions of the restrictive proximal head such that rotation of the corresponding bone anchor relative to the restrictive cap is restricted in at least one dimension.

11. The spinal system of claim 10, wherein the restrictive cap has opposed first and second at least partially curved side portions configured to seat a portion of the restrictive proximal head that has the generally spherical outer surface.

12. The spinal system of claim 11, wherein the opposed first and second curved side portions of the restrictive cap terminate at the two opposed restrictive side portions of the restrictive proximal head.

13. The spinal system of claim 11, wherein the first and second protrusions extend distally between the opposed first and second curved side portions of the restrictive cap.

14. The spinal system of claim 11, wherein distal ends of the first and second protrusions are at least partially tapered.

15. The spinal system of claim 11, further comprising a plurality of receiving members, each of the plurality of receiving members being configured to receive a corresponding one of the plurality of bone anchors therein and having two upright arms defining a recess therebetween for receiving the spinal rod therein, at least one of the plurality of receiving members being configured to seat the restrictive cap therein.

16. A surgical method, comprising:
advancing a distal shaft of at least a first bone anchor into a first vertebra, the first bone anchor having a proximal head disposed in a first receiving member, the first receiving member having two spaced apart upright arms defining a recess for receiving a spinal rod therebetween, and having a bore through a distal end thereof through which the distal shaft of the corresponding first bone anchor extends;
seating a first cap within the corresponding first receiving member, the first cap having side portions extending proximally on opposed sides of a received spinal rod above a center thereof; and
attaching first and second restrictor elements to the first cap, each of the first and second restrictor elements extending distally along the proximal head of the first bone anchor such that flat inner surfaces of the first and second restrictor elements engage with flat side portions of the proximal head of the first bone anchor.

17. The surgical method of claim 16, further comprising placing the spinal rod into the recess of the first receiving member to contact the first cap and to connect the first bone anchor with a second bone anchor to span vertebrae.

18. The surgical method of claim 17, further comprising engaging a first closure mechanism with the upright arms of the first receiving member to secure the spinal rod therein such that the side portions of the first cap are secured into restrictive engagement with the proximal head of the first bone anchor to restrict movement of the distal shaft of the first bone anchor relative to the first cap in at least a first direction and to allow movement in at least a second direction.

* * * * *